United States Patent
Raymond

(10) Patent No.: US 6,183,953 B1
(45) Date of Patent: Feb. 6, 2001

(54) **CHROMOSOMAL MUTAGENESIS IN *PICHIA METHANOLICA***

(75) Inventor: Christopher K. Raymond, Seattle, WA (US)

(73) Assignee: ZymoGenetics, Inc., Seattle, WA (US)

( * ) Notice: Under 35 U.S.C. 154(b), the term of this patent shall be extended for 0 days.

(21) Appl. No.: 09/001,141

(22) Filed: Dec. 30, 1997

Related U.S. Application Data

(60) Provisional application No. 60/058,822, filed on Sep. 15, 1997.

(51) Int. Cl.⁷ ........................................................ C12P 1/68
(52) U.S. Cl. ......................................................... 435/6
(58) Field of Search ...................... 435/6, 172.3

(56) References Cited

U.S. PATENT DOCUMENTS 5,135,868   8/1992   Cregg ................................. 435/255

FOREIGN PATENT DOCUMENTS

| | | | |
|---|---|---|---|
| 595 334 A2 | 5/1994 | (EP) | . |
| 92/17595 | 10/1992 | (WO) | . |
| 97/17450 | 5/1997 | (WO) | . |

OTHER PUBLICATIONS

Hiep et al., *Yeast* 9: 1189–1197, 1993.
Hiep et al., *Yeast* 9: 1251–1258, 1993.
Raymond et al., *Yeast* 14: 11–23, 1998.
Mezard et al., *Cell* 70: 659–670, 1992.
Rothstein, *Methods in Enzymology* 194: 281–301, 1991.
Rothstein, *Methods in Enzymology* 101: 202–211, 1983.

*Primary Examiner*—Lisa B. Arthur
(74) *Attorney, Agent, or Firm*—Gary E. Parker

(57) ABSTRACT

Methods for altering a selected chromosomal locus in *P. methanolica* cells and cells comprising such altered loci are disclosed. A linear DNA construct comprising (i) a segment comprising a portion of the target locus in which at least one nucleotide pair is altered and (ii) a selectable marker that complements adenine auxotrophy is introduced into cells auxotrophic for adenine. The cells are cultured under selective conditions, and cells in which the linear DNA construct has been chromosomally integrated by homologous recombination are identified. The cells are then cultured under conditions whereby cells auxotrophic for adenine can be identified, and a subset of such cells in which the altered locus has been chromosomally integrated are identified.

11 Claims, 6 Drawing Sheets

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 3077 base pairs
        (B) TYPE: nucleic acid
        (C) STRANDEDNESS: double
        (D) TOPOLOGY: linear (xi) SEQUENCE DESCRIPTION: SEQ ID NO:1:

```
CAGCTGCTCT GCTCCTTGAT TCGTAATTAA TGTTATCCTT TTACTTTGAA CTCTTGTCGG      60

TCCCCAACAG GGATTCCAAT CGGTGCTCAG CGGGATTTCC CATGAGGTTT TTGACAACTT     120

TATTGATGCT GCAAAAACTT TTTTAGCCGG GTTTAAGTAA CTGGGCAATA TTTCCAAAGG     180

CTGTGGGCGT TCCACACTCC TTGCTTTTCA TAATCTCTGT GTATTGTTTT ATTCGCATTT     240

TGATTCTCTT ATTACCAGTT ATGTAGAAAG ATCGGCAAAC AAAATATCAA CTTTTATCTT     300

GAACGCTGAC CCACGGTTTC AAATAACTAT CAGAACTCTA TAGCTATAGG GGAAGTTTAC     360

TGCTTGCTTA AAGCGGCTAA AAAGTGTTTG GCAAATTAAA AAAGCTGTGA CAAGTAGGAA     420

CTCCTGTAAA GGGCCGATTC GACTTCGAAA GAGCCTAAAA ACAGTGACTA TTGGTGACGG     480

AAAATTGCTA AAGGAGTACT AGGGCTGTAG TAATAAATAA TGGAACAGTG GTACAACAAT     540

AAAAGAATGA CGCTGTATGT CGTAGCCTGC ACGAGTAGCT CAGTGGTAGA GCAGCAGATT     600

GCAAATCTGT TGGTCACCGG TTCGATCCGG TCTCGGGCTT CCTTTTTTGC TTTTTCGATA     660

TTTGCGGGTA GGAAGCAAGG TCTAGTTTTC GTCGTTTCGG ATGGTTTACG AAAGTATCAG     720

CCATGAGTGT TTCCCTCTGG CTACCTAATA TATTTATTGA TCGGTCTCTC ATGTGAATGT     780

TTCTTTCCAA GTTCGGCTTT CAGCTCGTAA ATGTGCAAGA AATATTTGAC TCCAGCGACC     840

TTTCAGAGTC AAATTAATTT TCGCTAACAA TTTGTGTTTT TCTGGAGAAA CCTAAAGATT     900
```

-continued

```
TAACTGATAA GTCGAATCAA CATCTTTAAA TCCTTTAGTT AAGATCTCTG CAGCGGCCAG      960

TATTAACCAA TAGCATATTC ACAGGCATCA CATCGGAACA TTCAGAATGG ACTCGCAAAC     1020

TGTCGGGATT TTAGGTGGTG GCCAACTTGG TCGTATGATC GTTGAAGCTG CACACAGATT     1080

GAATATCAAA ACTGTGATTC TCGAAAATGG AGACCAGGCT CCAGCAAAGC AAATCAACGC     1140

TTTAGATGAC CATATTGACG GCTCATTCAA TGATCCAAAA GCAATTGCCG AATTGGCTGC     1200

CAAGTGTGAT GTTTTAACCG TTGAGATTGA ACATGTTGAC ACTGATGCGT TGGTTGAAGT     1260

TCAAAAGGCA ACTGGCATCA AAATCTTCCC ATCACCAGAA ACTATTTCAT TGATCAAAGA     1320

TAAATACTTG CAAAAAGAGC ATTTGATTAA GAATGGCATT GCTGTTGCCG AATCTTGTAG     1380

TGTTGAAAGT AGCGCAGCAT CTTTAGAAGA AGTTGGTGCC AAATACGGCT TCCCATACAT     1440

GCTAAAATCT AGAACAATGG CCTATGACGG AAGAGGTAAT TTTGTTGTCA AAGACAAGTC     1500

ATATATACCT GAAGCTTTGA AAGTTTTAGA TGACAGGCCG TTATACGCCG AGAAATGGGC     1560

TCCATTTTCA AAGGAGTTAG CTGTTATGGT TGTGAGATCA ATCGATGGCC AAGTTTATTC     1620

CTACCCAACT GTTGAAACCA TCCACCAAAA CAACATCTGT CACACTGTCT TTGCTCCAGC     1680

TAGAGTTAAC GATACTGTCC AAAAGAAGGC CCAAATTTTG GCTGACAACG CTGTCAAATC     1740

TTTCCCAGGT GCTGGTATCT TTGGTGTTGA AATGTTTTTA TTACAAAATG GTGACTTATT     1800

AGTCAACGAA ATTGCCCCAA GACCTCACAA TTCTGGTCAC TATACCATCG ACGCTTGTGT     1860

CACCTCGCAA TTTGAAGCTC ATGTTAGGGC CATTACTGGT CTACCCATGC CGAAGAACTT     1920

CACTTGTTTG TCGACTCCAT CTACCCAAGC TATTATGTTG AACGTTTTAG GTGGCGATGA     1980

GCAAAACGGT GAGTTCAAGA TGTGTAAAAG AGCACTAGAA ACTCCTCATG CTTCTGTTTA     2040

CTTATACGGT AAGACTACAA GACCAGGCAG AAAAATGGGT CACATTAATA TAGTTTCTCA     2100

ATCAATGACT GACTGTGAGC GTAGATTACA TTACATAGAA GGTACGACTA ACAGCATCCC     2160

TCTCGAAGAA CAGTACACTA CAGATTCCAT TCCGGGCACT TCAAGCAAGC CATTAGTCGG     2220

TGTCATCATG GGTTCCGATT CGGACCTACC AGTCATGTCT CTAGGTTGTA ATATATTGAA     2280

GCAATTTAAC GTTCCATTTG AAGTCACTAT CGTTTCCGCT CATAGAACCC CACAAAGAAT     2340

GGCCAAGTAT GCCATTGATG CTCCAAAGAG AGGGTTGAAG TGCATCATTG CTGGTGCTGG     2400

TGGTGCCGCT CATTTACCGG GAATGGTTGC GGCGATGACG CCGCTGCCTG TTATTGGTGT     2460

CCCTGTTAAA GGCTCTACTT TGGATGGTGT TGATTCACTA CACTCCATCG TTCAAATGCC     2520

AAGAGGTATT CCTGTTGCTA CTGTGGCTAT TAACAATGCT ACTAACGCTG CCTTGCTAGC     2580

TATCACAATC TTAGGTGCCG GCGATCCAAA TACTTGTCTG CAATGGAAGT TTATATGAAC     2640

AATATGGAAA ATGAAGTTTT GGGCAAGGCT GAAAAATTGG AAAATGGTGG ATATGAAGAA     2700

TACTTGAGTA CATACAAGAA GTAGAACCTT TTATATTTGA TATAGTACTT ACTCAAAGTC     2760

TTAATTGTTC TAACTGTTAA TTTCTGCTTT GCATTTCTGA AAAGTTTAAG ACAAGAAATC     2820

TTGAAATTTC TAGTTGCTCG TAAGAGGAAA CTTGCATTCA ATAACATTA ACAATAAATG      2880

ACAATAATAT ATTATTTCAA CACTGCTATA TGGTAGTTTT ATAGGTTTGG TTAGGATTTG     2940

AGATATTGCT AGCGCTTATC ATTATCCTTA ATTGTTCATC GACGCAAATC GACGCATTTC     3000

CACAAAAATT TTCCGAACCT GTTTTTCACT TCTCCAGATC TTGGTTTAGT ATAGCTTTTG     3060

ACACCTAATA CCTGCAG                                                    3077
```

(2) INFORMATION FOR SEQ ID NO:2:

(i) SEQUENCE CHARACTERISTICS:
        (A) LENGTH: 3386 base pairs (B) TYPE: nucleic acid
(C) STRANDEDNESS: double
(D) TOPOLOGY: linear (xi) SEQUENCE DESCRIPTION: SEQ ID NO:2:

```
GAATTCCTGC AGCCCGGGGG ATCGGGTAGT GGAATGCACG GTTATACCCA CTCCAAATAA       60
AAGTGTAGTA GCCGGACTGA AAGGTTTTAG GAGTCTGTTT GTTTGTTCAT GTGCATCATT      120
CCCTAATCTG TTAACAGTCT CGGAGTATAC AAAAAAGTAA GTCAAATATC AAGGTGGCCG      180
GGGGCAGCAT CGAGACTCGA GATGGTACAT ACTTAAAAGC TGCCATATTG AGGAACTTCA      240
AAGTTTTATC TGTTTTTAGA ATTAAAAGAC GATTGTTGTA ACAAAACGTT GTGCCTACAT      300
AAACTCAAAT TAATGGAAAT AGCCTGTTTT GAAAAATACA CCTTCTTAAG TACTGACAAA      360
GTTTTGTTAA ATGACTATCG AACAAGCCAT GAAATAGCAC ATTTCTGCCA GTCACTTTTA      420
ACACTTTCCT GCTTGCTGGT TGACTCTCCT CATACAAACA CCCAAAAGGG AAACTTTCAG      480
TGTGGGACA CTTGACATCT CACATGCACC CCAGATTAAT TTCCCCAGAC GATGCGGAGA       540
CAAGACAAAA CAACCCTTTG TCCTGCTCTT TTCTTTCTCA CACCGCGTGG GTGTGTGCGC      600
AGGCAGGCAG GCAGGCAGCG GGCTGCCTGC CATCTCTAAT CGCTGCTCCT CCCCCCTGGC      660
TTCAAATAAC AGCCTGCTGC TATCTGTGAC CAGATTGGGA CACCCCCCTC CCCTCCGAAT      720
GATCCATCAC CTTTTGTCGT ACTCCGACAA TGATCCTTCC CTGTCATCTT CTGGCAATCA      780
GCTCCTTCAA TAATTAAATC AAATAAGCAT AAATAGTAAA ATCGCATACA AACGTCATGA      840
AAAGTTTTAT CTCTATGGCC AACGGATAGT CTATCTGCTT AATTCCATCC ACTTTGGGAA      900
CCGCTCTCTC TTTACCCCAG ATTCTCAAAG CTAATATCTG CCCCTTGTCT ATTGTCCTTT      960
CTCCGTGTAC AAGCGGAGCT TTTGCCTCCC ATCCTCTTGC TTTGTTTCGG TTATTTTTTT     1020
TTCTTTTGAA ACTCTTGGTC AAATCAAATC AAACAAAACC AAACCTTCTA TTCCATCAGA     1080
TCAACCTTGT TCAACATTCT ATAAATCGAT ATAAATATAA CCTTATCCCT CCCTTGTTTT     1140
TTACCAATTA ATCAATCTTC AAATTTCAAA TATTTTCTAC TTGCTTTATT ACTCAGTATT     1200
AACATTTGTT TAAACCAACT ATAACTTTTA ACTGGCTTTA GAAGTTTTAT TTAACATCAG     1260
TTTCAATTTA CATCTTTATT TATTAACGAA ATCTTTACGA ATTAACTCAA TCAAAACTTT     1320
TACGAAAAAA AAATCTTACT ATTAATTTCT CAAAATGGCT ATTCCAGATG AATTTGATAT     1380
TATTGTTGTC GGTGGTGGTT CCACCGGTTG TGCTCTTGCT GGTAGATTAG GTAACTTGGA     1440
CGAAAACGTC ACAGTTGCTT TAATCGAAGG TGGTGAAAAC AACATCAACA ACCCATGGGT     1500
TTACTTACCA GGTGTTTATC CAAGAAACAT GAGATTAGAC TCAAAGACTG CTACTTTTTA     1560
CTCTTCAAGA CCATCACCAC ACTTGAACGG TAGAAGAGCT ATTGTTCCAT GTGCTAACAT     1620
CTTGGGTGGT GGTTCTTCCA TCAACTTCTT GATGTACACC AGAGCCTCTG CCTCCGATTA     1680
CGATGATTGG GAATCTGAAG GTTGGACTAC CGATGAATTA TTACCACTAA TGAAGAAGAT     1740
TGAAACTTAT CAAAGACCAT GTAACAACAG AGAATTGCAC GGTTTCGATG GTCCAATTAA     1800
GGTTTCATTT GGTAACTATA CTTATCCAAA CGGTCAAGAT TCATTAGAG CTGCCGAATC      1860
TCAAGGTATT CCATTTGTTG ATGATGCTGA AGATTTGAAA TGTTCCCACG GTGCTGAGCA     1920
CTGGTTGAAG TGGATCAACA GAGACTTAGG TAGAAGATCC GATTCTGCTC ATGCTTACAT     1980
TCACCCAACC ATGAGAAACA AGCAAAACTT GTTCTTGATT ACTTCCACCA AGTGTGAAAA     2040
GATTATCATT GAAACGGTG TTGCTACTGG TGTTAAGACT GTTCCAATGA AGCCAACTGG      2100
TTCTCCAAAG ACCCAAGTTG CTAGAACTTT CAAGGCTAGA AAGCAAATTA TTGTTTCTTG     2160
TGGTACTATC TCATCACCAT TAGTTTTGCA AAGATCTGGT ATCGGTTCCG CTCACAAGTT     2220
```

-continued

```
GAGACAAGTT GGTATTAAAC CAATTGTTGA CTTACCAGGT GTTGGTATGA ACTTCCAAGA   2280

TCACTACTGT TTCTTCACTC CATACCATGT CAAGCCAGAT ACTCCATCAT TCGATGACTT   2340

TGTTAGAGGT GATAAAGCTG TTCAAAAATC TGCTTTCGAC CAATGGTATG CTAACAAGGA   2400

TGGTCCATTA ACCACTAATG GTATTGAGGC AGGTGTTAAG ATTAGACCAA CTGAAGAAGA   2460

ATTAGCCACT GCTGATGACG AATTCAGAGC TGCTTATGAT GACTACTTTG GTAACAAGCC   2520

AGATAAGCCA TTAATGCACT ACTCTCTAAT TTCTGGTTTC TTTGGTGACC ACACCAAGAT   2580

TCCAAACGGT AAGTACATGT GCATGTTCCA CTTCTTGGAA TATCCATTCT CCAGAGGTTT   2640

CGTTCACGTT GTTTCTCCAA ACCCATACGA TGCTCCTGAC TTTGATCCAG GTTTCATGAA   2700

CGATCCAAGA GATATGTGGC CAATGGTTTG GTCTTACAAG AAGTCCAGAG AAACTGCCAG   2760

AAGAATGGAC TGTTTTGCCG GTGAAGTTAC TTCTCACCAC CCACACTACC CATACGACTC   2820

ACCAGCCAGA GCTGCTGACA TGGACTTGGA AACTACTAAA GCTTATGCTG GTCCAGACCA   2880

CTTTACTGCT AACTTGTACC ACGGTTCATG GACTGTTCCA ATTGAAAAGC CAACTCCAAA   2940

GAACGCTGCT CACGTTACTT CTAACCAAGT TGAAAAACAT CGTGACATCG AATACACCAA   3000

GGAGGATGAT GCTGCTATCG AAGATTACAT CAGAGAACAC ACTGAAACCA CATGGCATTG   3060

TCTTGGTACT TGTTCAATGG CTCCAAGAGA AGGTTCTAAG GTTGTCCCAA CTGGTGGTGT   3120

TGTTGACTCC AGATTAAACG TTTACGGTGT TGAAAAGTTG AAGGTTGCTG ATTTATCAAT   3180

TTGCCCAGAT AATGTTGGTT GTAACACTTA CTCTACTGCT TTGTTAATCG GTGAAAAGGC   3240

TTCTACCTTA GTTGCTGAAG ACTTGGGCTA CTCTGGTGAT GCTTTGAAGA TGACTGTTCC   3300

AAACTTCAAA TTGGGTACTT ATGAAGAAGC TGGTCTAGCT AGATTCTAGG GCTGCCTGTT   3360

TGGATATTTT TATAATTTTT GAGAGT                                      3386
```

(2) INFORMATION FOR SEQ ID NO:3:

(i) SEQUENCE CHARACTERISTICS:
        (A) LENGTH: 586 base pairs
        (B) TYPE: nucleic acid
        (C) STRANDEDNESS: double
        (D) TOPOLOGY: linear (xi) SEQUENCE DESCRIPTION: SEQ ID NO:3:

```
GATCTGATGC TGCGCATGCT TACATTCACC CAACTATGAG AAACAAGTCA AACTTATACT     60

TGATCACTTC CACTAAGGCT GATAAAGTTA TAATTGAAGA TGGAGTTGCA GCTGGTATTC    120

AAGTTGTTCC TTCCAAACCA TTGAACCCAG AAAAGCCGGC TGCCAAGATC TACAAGGCTA    180

GAAAGCAAAT CATTCTATCC TGTGGTACAA TTTCTACCCC GTTGGTCCTA CAAAGATCTG    240

GTATTGGCTC AGCTCATAAA TTAAGACAGG CAGGCATAAA ACCGATCGTT GACTTGCCAG    300

GAGTTGGTAT GAACTTCCAA GATCACTACT GCTTTTTCAC CCCATACCAT GTCAAGCCAG    360

ATACTCCTTC TTTTGATGAC TTTGCCAGAG GTGATAAGAC TGTTCAAAAA TCAGCTTTTG    420

ATCAATGGTA TGCTAACAAA GATGGTCCTT TAACCACTAA CGGTATTGAA GCTGGTGTTA    480

AGATTAGACC AACTGCTGAA GAACTGGCTA CTGCTGATGA AGATTTCCAA CTAGGCTACG    540

CTTCTTACTT TGAAAACAAG CCAGATAAAC CATTGATGCA TTACTC                  586
```

(2) INFORMATION FOR SEQ ID NO:4:

(i) SEQUENCE CHARACTERISTICS:
        (A) LENGTH: 38 base pairs
        (B) TYPE: nucleic acid
        (C) STRANDEDNESS: single

```
        (D) TOPOLOGY: linear (vii) IMMEDIATE SOURCE:
        (B) CLONE: ZC9080

(xi) SEQUENCE DESCRIPTION: SEQ ID NO:4:

TGATCACCTA GGACTAGTGA CAAGTAGGAA CTCCTGTA                                38

(2) INFORMATION FOR SEQ ID NO:5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (vii) IMMEDIATE SOURCE:
        (B) CLONE: ZC9079

(xi) SEQUENCE DESCRIPTION: SEQ ID NO:5:

CAGCTGCCTA GGACTAGTTT CCTCTTACGA GCAACTAGA                               39

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (vii) IMMEDIATE SOURCE:
        (B) CLONE: ZC8784

(xi) SEQUENCE DESCRIPTION: SEQ ID NO:6:

TGGTTGAAGT GGATCAA                                                      17

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (vii) IMMEDIATE SOURCE:
        (B) CLONE: ZC8787

(xi) SEQUENCE DESCRIPTION: SEQ ID NO:7:

GTGTGGTCAC CGAAGAA                                                      17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (vii) IMMEDIATE SOURCE:
        (B) CLONE: ZC9118

(xi) SEQUENCE DESCRIPTION: SEQ ID NO:8:

ACCTCCCAGT AAGCCTT                                                      17

(2) INFORMATION FOR SEQ ID NO:9:

(i) SEQUENCE CHARACTERISTICS:
        (A) LENGTH: 17 base pairs
        (B) TYPE: nucleic acid
```

```
            (C) STRANDEDNESS: single
            (D) TOPOLOGY: linear (vii) IMMEDIATE SOURCE:
            (B) CLONE: ZC9464

(xi) SEQUENCE DESCRIPTION: SEQ ID NO:9:

TTYGGNAART TYGAYGG                                                    17

(2) INFORMATION FOR SEQ ID NO:10:

(i) SEQUENCE CHARACTERISTICS:
            (A) LENGTH: 421 base pairs
            (B) TYPE: nucleic acid
            (C) STRANDEDNESS: double
            (D) TOPOLOGY: linear (ix) FEATURE:
            (A) NAME/KEY: Coding Sequence
            (B) LOCATION: 2...421
            (D) OTHER INFORMATION:

(xi) SEQUENCE DESCRIPTION: SEQ ID NO:10:

G GAA GGT AAC GTT TCT CAG GAT ACT TTA GCT TTA GGT GAT TTA GTT ATT      49
  Glu Gly Asn Val Ser Gln Asp Thr Leu Ala Leu Gly Asp Leu Val Ile
  1               5                  10                  15

CCA AAA CAA GAC TTT GCC GAA GCT ACT TCT GAG CCA GGT TTA GCA TTC        97
Pro Lys Gln Asp Phe Ala Glu Ala Thr Ser Glu Pro Gly Leu Ala Phe
            20                  25                  30

GCA TTT GGT AAA TTT GAT GGT ATT TTA GGT TTA GCT TAC GAT AGC ATT       145
Ala Phe Gly Lys Phe Asp Gly Ile Leu Gly Leu Ala Tyr Asp Ser Ile
        35                  40                  45

TCG GTC AAC AAG ATT GTT CCT CCT ATT TAT AAT GCT TTA AAC TTG GGT       193
Ser Val Asn Lys Ile Val Pro Pro Ile Tyr Asn Ala Leu Asn Leu Gly
    50                  55                  60

TTA TTA GAT GAA CCT CAA TTT GCC TTC TAC CTA GGT GAT ACT AAC ACC       241
Leu Leu Asp Glu Pro Gln Phe Ala Phe Tyr Leu Gly Asp Thr Asn Thr
65                  70                  75                  80

AAT GAA GAA GAT GGT GGT CTT GCC ACT TTT GGT GGT GTT GAT GAG TCC       289
Asn Glu Glu Asp Gly Gly Leu Ala Thr Phe Gly Gly Val Asp Glu Ser
                85                  90                  95

AAG TAT ACT GGT AAA GTT ACA TGG TTA CCA GTC AGA AGA AAG GCT TAC       337
Lys Tyr Thr Gly Lys Val Thr Trp Leu Pro Val Arg Arg Lys Ala Tyr
            100                 105                 110

TGG GAA GTT TCA TTA GAC GGT ATT TCA TTA GGT GAT GAA TAC GCG CCA       385
Trp Glu Val Ser Leu Asp Gly Ile Ser Leu Gly Asp Glu Tyr Ala Pro
        115                 120                 125

TTA GAA GGC CAT GGA GCT GCC ATT GAT ACA GGT ACC                       421
Leu Glu Gly His Gly Ala Ala Ile Asp Thr Gly Thr
    130                 135                 140

(2) INFORMATION FOR SEQ ID NO:11:

(i) SEQUENCE CHARACTERISTICS:
            (A) LENGTH: 140 amino acids
            (B) TYPE: amino acid
            (C) STRANDEDNESS: single
            (D) TOPOLOGY: linear (ii) MOLECULE TYPE: protein (v) FRAGMENT TYPE: internal (xi) SEQUENCE DESCRIPTION: SEQ ID NO:11:

Glu Gly Asn Val Ser Gln Asp Thr Leu Ala Leu Gly Asp Leu Val Ile
1               5                  10                  15
```

```
Pro Lys Gln Asp Phe Ala Glu Ala Thr Ser Glu Pro Gly Leu Ala Phe
        20                  25                  30

Ala Phe Gly Lys Phe Asp Gly Ile Leu Gly Leu Ala Tyr Asp Ser Ile
        35                  40                  45

Ser Val Asn Lys Ile Val Pro Pro Ile Tyr Asn Ala Leu Asn Leu Gly
50                      55                  60

Leu Leu Asp Glu Pro Gln Phe Ala Phe Tyr Leu Gly Asp Thr Asn Thr
65                  70                  75                  80

Asn Glu Glu Asp Gly Gly Leu Ala Thr Phe Gly Gly Val Asp Glu Ser
                85                  90                  95

Lys Tyr Thr Gly Lys Val Thr Trp Leu Pro Val Arg Arg Lys Ala Tyr
            100                 105                 110

Trp Glu Val Ser Leu Asp Gly Ile Ser Leu Gly Asp Glu Tyr Ala Pro
            115                 120                 125

Leu Glu Gly His Gly Ala Ala Ile Asp Thr Gly Thr
        130                 135                 140

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (vii) IMMEDIATE SOURCE:
        (B) CLONE: ZC9126

(xi) SEQUENCE DESCRIPTION: SEQ ID NO:12:

ATGTCAACAC ATTTACC                                               17

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (vii) IMMEDIATE SOURCE:
        (B) CLONE: ZC9741

(xi) SEQUENCE DESCRIPTION: SEQ ID NO:13:

CAYGGNACNC AYTGYGC                                               17

(2) INFORMATION FOR SEQ ID NO:14:

(i) SEQUENCE CHARACTERISTICS:
        (A) LENGTH: 368 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 1...366
        (D) OTHER INFORMATION:

(xi) SEQUENCE DESCRIPTION: SEQ ID NO:14:

GGG TCC GNA CNC ATG GTG TTT CTA AGA ATT GCC CAC ATT GTT GCC GTC    48
Gly Ser Xaa Xaa Met Val Phe Leu Arg Ile Ala His Ile Val Ala Val
 1               5                  10                  15

AAA GTT TTA AGA TCT AAC GGT TCA GGT TCT ATG CCC GAT GTT GTC AAG    96
Lys Val Leu Arg Ser Asn Gly Ser Gly Ser Met Pro Asp Val Val Lys
```

```
GGT GTT GAA TAT GCT CCC AAT GCT CAC CTT GCG GAA GCC AAG GCT AAC       144
Gly Val Glu Tyr Ala Pro Asn Ala His Leu Ala Glu Ala Lys Ala Asn
            35                  40                  45

AAG AGT GGT TTT AAA GGT TCT ACC GCG AAC ATG TCA TTA GGT GGT GGT       192
Lys Ser Gly Phe Lys Gly Ser Thr Ala Asn Met Ser Leu Gly Gly Gly
 50                  55                  60

AAA TCT CCA GCT TTA GAT ATG TCT GTT AAC GCT CCT GTT AAA GCA GGT       240
Lys Ser Pro Ala Leu Asp Met Ser Val Asn Ala Pro Val Lys Ala Gly
 65                  70                  75                  80

TTA CAC TTT GCC GTT ACC GCT GGT AAC GAT AAC ACT GAT GCA TGT AAC       288
Leu His Phe Ala Val Thr Ala Gly Asn Asp Asn Thr Asp Ala Cys Asn
                 85                  90                  95

TAT TCT CCA GCC ACT ACT GAA AAT ACT GTC ACT GTT GTT GCT TCC ACT       336
Tyr Ser Pro Ala Thr Thr Glu Asn Thr Val Thr Val Val Ala Ser Thr
                100                 105                 110

TTA TCT GAT TCG AGA GCT GAC ATG TCT AAC TC                            368
Leu Ser Asp Ser Arg Ala Asp Met Ser Asn
                115                 120
```

(2) INFORMATION FOR SEQ ID NO:15:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:15:

```
Gly Ser Xaa Xaa Met Val Phe Leu Arg Ile Ala His Ile Val Ala Val
 1                5                  10                  15

Lys Val Leu Arg Ser Asn Gly Ser Gly Ser Met Pro Asp Val Val Lys
                 20                  25                  30

Gly Val Glu Tyr Ala Pro Asn Ala His Leu Ala Glu Ala Lys Ala Asn
            35                  40                  45

Lys Ser Gly Phe Lys Gly Ser Thr Ala Asn Met Ser Leu Gly Gly Gly
 50                  55                  60

Lys Ser Pro Ala Leu Asp Met Ser Val Asn Ala Pro Val Lys Ala Gly
 65                  70                  75                  80

Leu His Phe Ala Val Thr Ala Gly Asn Asp Asn Thr Asp Ala Cys Asn
                 85                  90                  95

Tyr Ser Pro Ala Thr Thr Glu Asn Thr Val Thr Val Val Ala Ser Thr
                100                 105                 110

Leu Ser Asp Ser Arg Ala Asp Met Ser Asn
                115                 120
```

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ZC447

-continued (xi) SEQUENCE DESCRIPTION: SEQ ID NO:16:

TAACAATTTC ACACAGG                17

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (vii) IMMEDIATE SOURCE:
        (B) CLONE: ZC976

(xi) SEQUENCE DESCRIPTION: SEQ ID NO:17:

CGTTGTAAAA CGACGGCC               18

CHROMOSOMAL MUTAGENESIS IN *PICHIA METHANOLICA*

This application claims the benefit of provisional application Ser. No. 60/058,822, filed Sep. 15, 1997.

BACKGROUND OF THE INVENTION

Methylotrophic yeasts are those yeasts that are able to utilize methanol as a sole source of carbon and energy. Species of yeasts that have the biochemical pathways necessary for methanol utilization are classified in four genera, Hansenula, Pichia, Candida, and Torulopsis. These genera are somewhat artificial, having been based on cell morphology and growth characteristics, and do not reflect close genetic relationships (Billon-Grand, *Mycotaxon* 35:201–204, 1989; Kurtzman, *Mycologia* 84:72–76, 1992). Furthermore, not all species within these genera are capable of utilizing methanol as a source of carbon and energy. As a consequence of this classification, there are great differences in physiology and metabolism between individual species of a genus.

Methylotrophic yeasts are attractive candidates for use in recombinant protein production systems. Some methylotrophic yeasts have been shown to grow rapidly to high biomass on minimal defined media. Certain genes of methylotrophic yeasts are tightly regulated and highly expressed under induced or de-repressed conditions, suggesting that promoters of these genes might be useful for producing polypeptides of commercial value. See, for example, Faber et al., *Yeast* 11:1331, 1995; Romanos et al., *Yeast* 8:423, 1992; and Cregg et al., *Bio/Technology* 11:905, 1993.

Development of methylotrophic yeasts as hosts for use in recombinant protein production systems has been slow, due in part to a lack of suitable materials (e.g., promoters, selectable markers, and mutant host cells) and methods (e.g., transformation techniques). The most highly developed methylotrophic host systems utilize *Pichia pastoris* and *Hansenula polymorpha* (Faber et al., *Curr. Genet.* 25:305–310, 1994; Cregg et al., ibid.; Romanos et al., ibid.; U.S. Pat. No. 4,855,242; U.S. Pat. No. 4,857,467; U.S. Pat. No. 4,879,231; and U.S. Pat. No. 4,929,555).

More recently, materials and techniques useful for producing foreign proteins in *Pichia methanolica* have been developed (WIPO Publication WO 9717450). However, there remains a need in the art for additional techniques that can be used to manipulate the genome of *P. methanolica* so as to expand our understanding of this organism and produce strains that can be used in large-scale protein production systems.

One such needed tool is a technique for directed mutagenesis of *P. methanolica*. Directed mutagenesis allows the introduction of mutations into predetermined genomic loci, permitting the selective alteration of gene activity. Useful alterations include, for example, mutation of promoter sequences to increase gene expression, introduction of heterologous genes at particular sites, and generation of protease deficiencies and auxotrophies. Techniques developed for the budding yeast *Saccharomyces cerevisiae* are unsuitable for *P. methanolica*. For example, the "pop-in/pop-out" method developed by Scherer and Davis (*Proc. Natl. Acad. Sci. USA* 76:1035, 1979) and summarized by Rothstein (*Methods Enzymol.* 194:281, 1991) requires a selection against the presence of the URA3 marker, such as by addition of 5-FOA (5 fluoro orotic acid) to the culture medium. This method is unsuitable with *P. methanolica* because the cells are resistant to 5 fluoro-orotic acid (5-FOA), and no *P. methanolica* URA marker is available. The present invention provides methods for producing directed mutations in the genome of *P. methanolica*, cells having such mutations, and other, related advantages.

SUMMARY OF THE INVENTION

The present invention provides a method for altering a chromosomal locus of *Pichia methanolica* cells, comprising the steps of: (a) selecting a target chromosomal locus of the cells; (b) providing a population of *P. methanolica* cells each comprising a chromosomal copy of the selected target locus, wherein the cells are auxotrophic for adenine; (c) introducing into the cells a linear DNA construct comprising (i) a segment comprising a portion of the target chromosomal locus in which at least one nucleotide pair is altered, and (ii) a selectable marker that complements adenine auxotrophy; (d) culturing the cells from step (c) under conditions that are selective for the presence in the cells of the selectable marker; (e) identifying a subset of the cultured cells in which the segment of the DNA construct and the selectable marker have been chromosomally integrated by homologous recombination, resulting in tandem duplication of the target chromosomal locus; (f) culturing the identified subset of cells under conditions wherein cells prototrophic for adenine grow and exhibit a first phenotype, and cells auxotrophic for adenine grow and exhibit a second phenotype; (g) recovering cells that are auxotrophic for adenine; and (h) identifying a subset of the auxotrophic cells in which the segment of the DNA construct has been chromosomally integrated, whereby the target chromosomal locus is altered. Within one embodiment of the invention, a plurality of nucleotide pairs of the portion of the chromosomal locus are altered. Within a related embodiment, from 1 kbp to 2 kbp of the portion of the chromosomal locus is altered. Within another embodiment, the alteration is a deletion of at least one nucleotide pair. Within further embodiments, the target chromosomal locus encodes a protease, such as proteinase A or proteinase B, an alcohol oxidase, or a nutritional marker.

Within the method disclosed above, steps (a) through (h) can be repeated, whereby two or more chromosomal loci are altered. Within certain embodiments of the invention, a chromosomal locus encoding a protease and a second chromosomal locus encoding an alcohol oxidase are altered.

The invention also provides a *Pichia methanolica* cell produced by the method disclosed above.

These and other aspects of the invention will become evident upon reference to the following detailed description and the attached drawings.

DETAILED DESCRIPTION OF THE INVENTION

Figure 1:
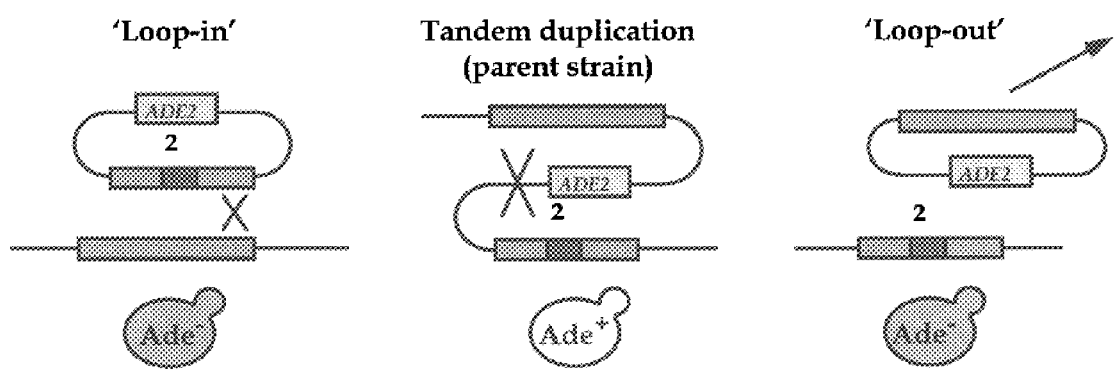
FIG. 1 illustrates one embodiment of the invention whereby a gene deletion is introduced into a chromosomal locus.

A "chromosomal locus" is a region of DNA found in the genome of a cell. A chromosomal locus can, but need not, comprise one or more genes.

A "DNA construct" is a DNA molecule, either single- or double-stranded, that has been modified through human intervention to contain segments of DNA combined and juxtaposed in an arrangement not existing in nature. "Homologous recombination" is genetic recombination between pairs of DNA molecules having regions of sequence identity.

"Linear DNA" denotes DNA molecules having free 5' and 3' ends, that is non-circular DNA molecules. Linear DNA can be prepared from closed circular DNA molecules, such as plasmids, by enzymatic digestion or physical disruption.

A "nutritional marker" is a gene that encodes a protein required for biosynthesis of a necessary nutrient. Nutritional markers include genes encoding enzymes required for amino acid and nucleotide biosynthesis.

The term "operably linked" indicates that DNA segments are arranged so that they function in concert for their intended purposes, e.g., transcription initiates in the promoter and proceeds through the coding segment to the terminator.

"Selective" culture conditions are those conditions that provide for preferential growth of cells having a predetermined phenotype. This phenotype is commonly the result of the expression of a gene that has been introduced into the cell (or introduced into a parent cell) to complement a mutation.

"Tandem duplication" of a chromosomal locus denotes the introduction into a chromosome of a second copy of an existing locus whereby the second copy is inserted into the original copy by homologous recombination between the chromosomal locus and the counterpart locus on an exogenously supplied DNA molecule. Duplication may result in alteration of the original copy of the locus, such as when an altered form of the locus is introduced into the cell and incorporated into the chromosome. The resulting configuration of the duplicated locus is determined by the nature of any introduced alteration(s) and the presence or absence of additional DNA linked to the introduced copy of the locus. Within the methods of the present invention, tandem duplication of a target locus will generally introduce a disrupted copy into the locus and insert a selectable marker and other vector sequences between the two copies of the locus.

The present invention provides methods for introducing alterations (mutations) into chromosomal loci of *Pichia methanolica*. Strains of *Pichia methanolica* for use within the invention can be obtained from the American Type Culture Collection (Rockville, Md.) and other repositories. These strains can be used as parent strains for the production of strains having a desired chromosomal mutation. Those skilled in the art will recognize that both parent and mutant strains can be further mutagenized according to known techniques in order to obtain strains having desired genotypes (e.g., ade⁻). One can thereby obtain strains having defined nutritional requirements, metabolic defects, etc. It is thus possible to design strains of *P. methanolica* for use in, for example, large-scale fermentation for protein production.

Of particular interest for protein production systems are strains of *P. methanolica* that are deficient in vacuolar protease activity. In yeasts, the major store of proteolytic activity is located within the lumen of the vacuolar compartment (Jones, *Methods Enzymol.* 194:428–453, 1991). These proteases are released into the fermentation broth by spontaneous and inevitable cell lysis and are further liberated during cell breakage that is required to release intracellulary produced proteins in laboratory or industrial production, thereby limiting recovery of intact protein. It is therefore desirable to reduce or eliminate vacuolar protease activity in production strains. Vacuolar protease genes of particular interest in this regard include the PEP4 gene, which encodes proteinase A, and the PRB1 gene, which encodes proteinase B. The designations of these genes were based on functional equivalence to the *Saccharomyces cerevisiae* genes of the same names and by a high degree of sequence identity (70%) between the encoded *P. methanolica* and *S. cerevisiae* proteins. Although other vacuolar proteases (e.g., carboxypeptidase Y) are present in *P. methanolica*, the PEP4 and PRB1 gene products activate the other vacuolar proteases, so that negation of PEP4 and PRB1 functions results in a strain that is effectively vacuolar protease negative.

The preparation of vacuolar protease-deficient strains of *P. methanolica* as disclosed herein serves to illustrate the methods of the present invention. Those skilled in the art will recognize that the methods disclosed can be readily applied to the alteration of other chromosomal loci of *P. methanolica*. Other loci of interest in this regard include, without limitation, genes encoding alcohol oxidase (AUG1 and AUG2 genes), golgi endoprotease (orthologs of *S. cerevisiae* KEX2 and YAP3 genes), nutritional markers (e.g., HIS3, LEU2), β-1,3-glucanase, and mating pheromones; the HO gene; and other genes encoding proteins of the methanol utilization pathway (e.g., genes encoding dihydroxyacetone synthase, formate dehydrogenase, and catalase).

Within the present invention, an alteration within a selected target chromosomal locus is generated through a process of loop-in/loop-out mutagenesis, whereby an altered copy of the target chromosomal locus is used to replace the endogenous copy within the genome. One example of this method is illustrated in FIG. 1. A linear DNA construct comprising (1) a portion of the selected target chromosomal locus in which at least one nucleotide pair is altered (indicated by "Δ" in FIG. 1), and (2) a selectable marker (ADE2 in FIG. 1) is introduced into the cells. The cells are cultured under selective conditions, then a subset of the cells is identified, in which the altered chromosomal locus portion and selectable marker have been chromosomally integrated by homologous recombination. The recombination event results in tandem duplication of the target chromosomal locus. Within FIG. 1, the introduced DNA is shown as a circular molecule, because *P. methanolica* recircularizes the linear DNA after transformation. As shown in FIG. 1, recombination between the introduced and chromosomal copies of the target locus results in duplication of the target locus, with the selectable marker interposed between the two copies. The cells are then cultured under conditions in which cells which undergo a spontaneous loop-out event can be identified. This loop-out event results from a second homologous recombination between the two copies of the target locus. Two outcomes are possible: the looping out of the wild-type copy of the locus, illustrated in FIG. 1; and the looping out of the altered copy (not shown), which regenerates the parental state.

An alteration is created in a cloned chromosomal locus or portion thereof, for example a cloned vacuolar protease gene, by conventional methods of DNA manipulation, such as restriction endonuclease digestion and re-ligation, insertional mutagenesis, polymerase chain reaction (PCR; Mullis, U.S. Pat. No. 4,683,202), site-directed mutagenesis (Sambrook et al., *Molecular Cloning: A Laboratory Manual*, 2nd ed., Cold Spring Harbor Laboratory Press, 1989, 15.3–15.113), or other methods known in the art. The altered copy of the locus is then introduced into the cell as a linear DNA construct that further comprises a selectable marker that complements an auxotrophic mutation in the cell. It is preferred that the cell be auxotrophic for adenine and that the selectable marker complements adenine auxotrophy. A preferred such marker is the *P. methanolica* ADE2 gene, a representative sequence of which is shown in SEQ ID NO:1, or a functional portion thereof.

A population of *P. methanolica* cells, each comprising a chromosomal copy of the target locus, is prepared. Strains of *P. methanolica* are available from publicly accessible depositories, such as the American Type Culture Collection, Rockville, Md., USA. Cells are cultured in a suitable medium, such as YEPD. If necessary, the cells can be mutagenized to obtain the desired auxotrophy. To prepare auxotrophic mutants of *P. methanolica*, cells are first exposed to mutagenizing conditions, i.e., environmental conditions that cause genetic mutations in the cells. Methods for mutagenizing cells are well known in the art and include chemical treatment, exposure to ultraviolet light, exposure to X-rays, and retroviral insertional mutagenesis. Chemical mutagens include ethylmethane sulfonate (EMS), N-methyl-N'-nitro-N-nitrosoguanidine, 2-methoxy-6-chloro-9-[3-(ethyl-2-chloroethyl) amino-propylamino] acridine.2HCl, 5-bromouracil, acridine, and aflatoxin. See Lawrence, *Methods Enzymol.* 194:273–281, 1991. The proportion of mutagenized cells obtained is a function of the strength or amount of mutagenizing agent to which the cells are exposed. A low level of mutagen produces a small proportion of mutant cells. Higher levels of mutagen produce a higher proportion of mutant cells, but also mutagenize more loci and kill more cells. It is therefore necessary to balance these outcomes so that a reasonable number of singly mutated cells is obtained. Balancing is generally done empirically by exposing cells to different conditions to establish a killing curve. In general, the cells are exposed to mutagenizing conditions and cultured for one day, after which they are tested for viability according to standard assay methods. In general, it is preferred to use a level of mutagenesis that results in 10–20% mortality, although one skilled in the art will recognize that this value can be adjusted as necessary, for example if working with a very large number of cells.

Mutagenized cells are then cultured in a rich medium to allow mutations to become established and replicated in at least a portion of the cell population. This step allows cells in which the genome has been altered to replicate the mutation and pass it on to their progeny, thereby establishing the mutation within the population.

The cells are then transferred to a culture medium deficient in assimilable nitrogen so that cellular nitrogen stores are depleted. By "deficient in assimilable nitrogen" it is meant that the medium lacks an amount of nitrogen sufficient to support growth of the cells. Depletion of cellular nitrogen stores will generally require about 12 to 24 hours of incubation, with 16 hours being sufficient under common conditions. Following depletion of nitrogen stores, the cells are cultured in a defined culture medium comprising an inorganic nitrogen source and an amount of an antifungal antibiotic sufficient to kill growing *P. methanolica* cells. The antibiotic nystatin (mycostatin) is preferred. Preferred inorganic nitrogen sources are those comprising ammonium ions, such as ammonium sulfate. In general, the medium will contain 10–200 mM ammonium, preferably about 60 mM ammonium. Nystatin is included at a concentration of 0.1 to 100 mg/l, preferably 0.5 to 20 mg/L, more preferably about 2 mg/L (10 units/L). Treatment with nystatin is carried out for ten minutes to six hours, preferably about 1 hour. Those skilled in the art will recognize that the actual antibiotic concentration and exposure time required to kill prototrophic cells can be readily determined empirically, and certain adjustments may be necessary to compensate for variations in specific activity between individual batches of antibiotic. By depleting cellular nitrogen stores and then culturing the cells in a defined medium containing an inorganic nitrogen source and antibiotic, cells that are auxotrophic for amino acid or nucleotide biosynthesis remain alive because they cannot grow in the defined medium. Growing cells are killed by the antibiotic. Following the antibiotic treatment, the cells are transferred to a rich culture medium.

A significant proportion of cells that survive nystatin treatment are prototrophs. Auxotrophic mutants within the surviving population are identified and characterized by determining the nutrient requirements of the cells. Replica plating is commonly used for this determination. Cells are plated on both rich medium and media lacking specific nutrients. Cells that do not grow on particular plates are auxotrophic for the missing nutrient. Complementation analysis can be used for further characterization.

Alteration of a chromosomal locus in the host cells is achieved by homologous recombination between the cellular chromosomal locus and a homologous DNA segment introduced into the cell. The homologous segment comprises at least a portion of the target locus that has been cloned in a DNA construct, typically a plasmid. At least one nucleotide pair in the cloned portion of the locus is altered by deletion, substitution, or insertion, with deletion being preferred. Combinations of alterations can also be made, resulting in, for example, a cloned locus from which a first region has been deleted and a second region has been interrupted by insertion. Such alterations will preferably eliminate one or more active site amino acid residues of the protein product of the target locus, thereby detroying protein activity. Frameshift mutations, for example, can be generated by deleting a partial codon, thus deletion of a single nucleotide, and preferably at least four nucleotides, can produce the desired inactivating mutation. It is preferred to delete or otherwise alter at least most of the open reading frame (ORF) of the cloned locus. Alterations can extend beyond the ORF into the promoter or terminator or both, but it is preferred not to disrupt adjacent gene sequences. In practice, the actual extent of any deletion will usually be based on the locations of convenient restriction enzyme recognition sites. The alteration will be flanked on each end by sufficient sequence to facilitate homologous recombination with the target locus. Although as little as two base pairs of sequence identity has been reported to be adequate (Mézard et al., *Cell* 70:659–670, 1992), it is preferred to provide at least ten base pairs of unaltered target locus sequence at each end of the alteration. It is preferred that the alteration be flanked by at least 100 base pairs, up to as much as 10 kilobase pairs, of unaltered sequence at each end. In any event, the DNA construct must contain sufficient amounts of sequence homologous to the target cell genome to permit homologous recombination at the target locus. In practice, deletions or other alterations will commonly cover from about 1 kb to about 2 kb of the locus of interest, although larger regions of up to 10 kb or more, depending on the size of the target locus, can be altered. Within one embodiment of the invention, the object of the alteration is to effectively eliminate the activity of the target locus, and it is preferred to do so in a way that will minimize or eliminate the possibility of reversions or other compensating mutations. Within another embodiment, the object of the alteration is to insert a gene or genes coding for a new function. Application of the methods of the present invention to specific target loci is within the level of ordinary skill in the art.

As noted above, the DNA construct to be introduced into the cell will comprise, in addition to the altered locus portion, a selectable marker. The presence of the selectable marker facilitates the identification and selection of integrative transformants by allowing cells expressing the marker to grow under conditions in which cells lacking the marker cannot multiply. The general principles of selection are well known in the art. Commonly used selectable markers are genes that encode enzymes required for the synthesis of amino acids or nucleotides. Cells having mutations in these genes cannot grow in media lacking the specific amino acid or nucleotide unless the mutation is complemented by the selectable marker. Use of such "selective" culture media ensures the stable maintenance of the heterologous DNA within the host cell. A preferred selectable marker of this type for use in *Pichia methanolica* is a *P. methanolica* ADE2 gene, which encodes phosphoribosyl-5-aminoimidazole carboxylase (AIRC; EC 4.1.1.21). The ADE2 gene, when transformed into an ade2 host cell, allows the cell to grow in the absence of adenine. The coding strand of a representative *P. methanolica* ADE2 gene sequence is shown in SEQ ID NO:1. The sequence illustrated includes 1006 nucleotides of 5' non-coding sequence and 442 nucleotides of 3' non-coding sequence, with the initiation ATG codon at nucleotides 1007–1009. Within a preferred embodiment of the invention, a DNA segment comprising nucleotides 407–2851 is used as a selectable marker, although longer or shorter segments can be used as long as the coding portion is operably linked to promoter and terminator sequences. Those skilled in the art will recognize that this and other sequences provided herein represent single alleles of the respective genes, and that allelic variation is expected to exist. Any functional ADE2 allele can be used as a selectable marker. Other nutritional markers that can be used within the present invention include the *P. methanolica* ADE1, HIS3, and LEU2 -genes, which allow for selection in the absence of adenine, histidine, and leucine, respectively. *P. methanolica* genes can be cloned on the basis of homology with their counterpart *Saccharomyces cerevisiae* genes. Heterologous genes, such as genes from other fungi, can also be used as selectable markers.

DNA to be introduced into *P. methanolica* is first linearized, such as by digestion with one or more restriction endonucleases. Linearization increases the efficiency of transformation. Linearization by digestion with sequence-specific endonucleases also allows the specific removal of exogenous sequences so that only the desired DNA sequences are introduced into the cell.

DNA can be introduced into *P. methanolica* cells by any of several known methods, including lithium transformation (Hiep et al., *Yeast* 9:1189–1197, 1993; Tarutina and Tolstorukov, *Abst. of the 15th International Specialized Symposium on Yeasts,* Riga (USSR), 1991, 137; Ito et al., *J. Bacteriol.* 153:163, 1983; Bogdanova et al., *Yeast* 11:343, 1995), spheroplast transformation (Beggs, *Nature* 275:104, 1978; Hinnen et al., *Proc. Natl. Acad. Sci. USA* 75:1929, 1978; Cregg et al., *Mol. Cell. Biol.* 5:3376, 1985), freeze-thaw polyethylene glycol transformation (Pichia Expression Kit Instruction Manual, Invitrogen Corp., San Diego, Calif., Cat. No. K1710-01), or electroporation, the latter being preferred. Electroporation is the process of using a pulsed electric field to transiently permeabilize cell membranes, allowing macromolecules, such as DNA, to pass into cells. Electroporation has been described for use with mammalian (e.g., Neumann et al., *EMBO J.* 1:841–845, 1982) and fungal (e.g., Meilhoc et al., *Bio/Technology* 8:223–227, 1990) host cells. However, the actual mechanism by which DNA is transferred into the cells is not well understood. For transformation of *P. methanolica*, it has been found that electroporation is surprisingly efficient when the cells are exposed to an exponentially decaying, pulsed electric field having a field strength of from 2.5 to 4.5 kV/cm and a time constant ($\tau$) of from 1 to 40 milliseconds. The time constant $\tau$ is defined as the time required for the initial peak voltage $V_0$ to drop to a value of $V_0/e$. The time constant can be calculated as the product of the total resistance and capacitance of the pulse circuit, i.e., $\tau = R \times C$. Typically, resistance and capacitance are either preset or may be selected by the user, depending on the electroporation equipment selected. In any event, the equipment is configured in accordance with the manufacturer's instructions to provide field strength and decay parameters as disclosed above. Electroporation equipment is available from commercial suppliers (e.g., BioRad Laboratories, Hercules, Calif.).

Cells into which the altered locus has been introduced are then cultured under conditions that are selective for the presence of the selectable marker as disclosed above.

Cells obtained after culturing in selective conditions are then analyzed to identify a subset of the cells in which the altered locus and the selectable marker have been chromosomally integrated by homologous recombination. Tandem duplication of the target chromosomal locus resulting from homologous recombination can be detected by structural changes at the target locus. Transformants that have undergone the desired homologous recombination event are identified by known methods, such as Southern blotting (see, e.g., Strathern and Higgins, *Methods Enzymol.* 194:319–329, 1991) or polymerase chain reaction. For Southern blotting, genomic DNA is prepared from transformants and control cells, digested with one or more restriction enzymes, transferred to a blot, and probed to detect a change in the restriction pattern following transformation. Reagents, materials, equipment and protocols for preparing and probing blots are available from commercial suppliers. In the alternative, the target region can be amplified by PCR and analyzed by gel electrophoresis to detect a size change.

As disclosed in more detail in Example 3, below, selection for the Ade$^+$ phenotype gave rise to two classes of transformants. One class arose quickly as white colonies on the primary translation plate. The second class became evident as rapidly growing white papillae on the edges of unstable, pink transformants. Analysis by Southern blotting showed that 19% of the first class of transformants had undergone homologous recombination, while 89% of the cells from the white papillae were homologous recombinants.

Cells having the desired tandem duplication are then cultured under conditions wherein prototrophic cells grow and exhibit a first phenotype, and auxotrophic cells grow and exhibit a second phenotype. The culture conditions are non-selective to allow for spontaneous looping-out of the integrated selectable marker and wild-type copy of the target locus as shown in FIG. 1. This phenotypic differentiation is achieved by, for example, culturing the cells in rich media containing limiting amounts of adenine, so that ade$^-$ cells can grow, but the ade$^-$ colonies are pink in color.

Auxotrophic (ade$^-$) cells are then recovered. A subset of the auxotrophic cells in which the altered locus has been chromosomally integrated is then identified using conventional analytic methods, such as PCR or restriction enzyme digestion and Southern blotting as disclosed above. Mitotic recombination can result in looping out of either copy of the tandemly duplicated locus. The desired cells are those in which the selectable marker and wild-type chromosomal sequences have been looped out, leaving a single, disrupted copy of the target chromosomal locus (FIG. 1).

The presence of an alteration in the target chromosomal locus can be further confirmed by assays, including activity assays, endonuclease digestion and Southern blot analysis, and growth phenotype assays. In certain instances it may be necessary to alter a plurality of loci in order to obtain the desired phenotype. For example, vacuolar protease deficiency is obtained by eliminating proteinase A and proteinase B activities. Vacuolar protease activity (and therefore vacuolar protease deficiency) is measured using any of several known assays. Preferred assays are those developed for *Saccharomyces cerevisiae* and disclosed by Jones, *Methods Enzymol.* 194:428–453, 1991 (incorporated herein by reference). A preferred such assay is the APE overlay assay, which detects activity of carboxypeptidase Y (CpY). Briefly, the assay detects the carboxypeptidase Y-mediated release of β-naphthol from an ester, which results in the formation of an isoluble red dye by the reaction of the β-naphthol with the diazonium salt Fast Garnet GBC. Colonies are overlayed with a 0.6% agar solution of N-Acetyl-DL-phenylalanine β-naphthyl ester containing 1 mg/ml dimethylformamide. After the overlay hardens, the plates are flooded with a solution of Fast Garnet GBC (5 mg/ml in 0.1 M Tris-HCl, pH 7.3–7.5). Within a few minutes, Cpy$^+$ colonies turn red. Carboxypeptidase Y activity can also be detected by the well test, in which cells are distributed into wells of a microtiter test plate and incubated in the presence of N-benzoyl-L-tyrosine p-nitroanilide (BTPNA) and dimethylformamide. The cells are permeabilized by the dimethylformamide, and CpY in the cells cleaves the amide bond in the BTPNA to give the yellow product p-nitroaniline. Assays for CpY will detect any mutation that reduces protease activity so long as that activity ultimately results in the reduction of CpY activity. Proteinase B activity can be detected using an HPA overlay test, which detects the solubilization of Hide Powder Azure by proteinase B. Colonies producing the enzyme are surrounded by a clear halo, while deficient mutants remain covered. Carboxypeptidase S can be assayed using a well test that detects the release of leucine from carbobenzoxyglycyl-L-leucine. In the presence of L-amino-acid oxidase, $H_2O_2$ is produced by the oxidation of the free leucine. The $H_2O_2$ reacts with o-dianisidine dihydrochloride in the presence of peroxidase to produce oxidized dianisidine, which is dark brown. Additional assays are known and within the level of ordinary skill in the art to perform.

Strains having altered target loci are useful as hosts for the expression of heterologous genes. Methods for introducing heterologous DNAs into *P. methanolica*, culturing the cells, and expressing heterologous genes are disclosed in WIPO Publication WO 9717450. Cells to be transformed with heterologous DNA will have a mutation that can be complemented by a selectable marker on the heterologous DNA molecule. Because the selectable marker is excised from the chromosome in the loop-out step disclosed above, it is convenient to use the same marker in introducing a gene encoding a protein of interest. Those skilled in the art will recognize, however, that a different marker can also be used. Selection of particular cell and marker combinations is within the level of ordinary skill in the art.

Proteins that can be produced in *P. methanolica* include proteins of industrial and pharmaceutical interest. Such proteins include higher eukaryotic proteins from plants and animals, particularly vertebrate animals such as mammals, although certain proteins from microorganisms are also of great value. Examples of proteins that can be prepared include enzymes such as lipases, cellulases, and proteases; enzyme inhibitors, including protease inhibitors; growth factors such as platelet derived growth factor, fibroblast growth factors, and epidermal growth factor; cytokines such as erythropoietin and thrombopoietin; and hormones such as insulin, leptin, and glucagon.

DNA molecules for use in transforming *P. methanolica* will commonly be prepared as double-stranded, circular plasmids, which are preferably linearized prior to transformation. For polypeptide or protein production, the DNA molecules will include, in addition to the selectable marker disclosed above, an expression casette comprising a transcription promoter, a DNA segment (e.g., a cDNA) encoding the polypeptide or protein of interest, and a transcription terminator. These elements are operably linked to provide for transcription of the DNA segment of interest. It is preferred that the promoter and terminator be that of a *P. methanolica* gene. Useful promoters include those from constitutive and methanol-inducible promoters. Promoter sequences are generally contained within 1.5 kb upstream of the coding sequence of a gene, often within 1 kb or less. In general, regulated promoters are larger than constitutive promoters due the presence of regulatory elements. Methanol-inducible promoters, which include both positive and negative regulatory elements, may extend more than 1 kb upstream from the initiation ATG. Promoters are identified by function and can be cloned according to known methods.

A particularly preferred methanol-inducible promoter is that of a *P. methanolica* alcohol utilization gene. A representative coding strand sequence of one such gene, AUG1, is shown in SEQ ID NO:2. Within SEQ ID NO:2, the initiation ATG codon is at nucleotides 1355–1357. Nucleotides 1–23 of SEQ ID NO:2 are non-AUG1 polylinker sequence. It is particularly preferred to utilize as a promoter a segment comprising nucleotides 24–1354 of SEQ ID NO:2, although additional upstream sequence can be included. *P. methanolica* contains a second alcohol utilization gene, AUG2, the promoter of which can be used within the present invention. A partial DNA sequence of one AUG2 clone is shown in SEQ ID NO:3. AUG2 promoter segments used within the present invention will generally comprise nucleotides 91–169 of SEQ ID NO:3, although small truncations at the 31 end would not be expected to negate promoter function. Other useful promoters include those of the dihydroxyacetone synthase (DHAS), formate dehydrogenase (FMD), and catalase (CAT) genes. Genes encoding these enzymes from other species have been described, and their sequences are available (e.g., Janowicz et al., *Nuc. Acids Res.* 13:2043, 1985; Hollenberg and Janowicz, EPO publication 0 299 108; Didion and Roggenkamp, *FEBS Lett.* 303:113, 1992). Genes encoding these proteins can be cloned by using the known sequences as probes, or by aligning known sequences, designing primers based on the alignment, and amplifying *P. methanolica* DNA by the polymerase chain reaction.

Constitutive promoters are those that are not activated or inactivated by environmental conditions; they are always transcriptionally active. Preferred constitutive promoters for use within the present invention include those from glyceraldehyde-3-phosphate dehydrogenase, triose phosphate isomerase, and phosphoglycerate kinase genes of *P. methanolica*. These genes can be cloned as disclosed above or by complementation in a host cell, such as a *Saccharomyces cerevisiae* cell, having a mutation in the counterpart gene. Mutants of this type are well known in the art. See, for example, Kawasaki and Fraenkel, *Biochem. Biophys. Res. Comm.* 108:1107–1112, 1982; McKnight et al., *Cell* 46:143–147, 1986; Aguilera and Zimmermann, *Mol. Gen. Genet.* 202:83–89, 1986.

The DNA constructs used within the present invention may further contain additional elements, such as an origin of replication and a selectable marker that allow amplification and maintenance of the DNA in an alternate host (e.g., *E. coli*). To facilitate integration of the DNA into the host chromosome, it is preferred to have the entire expression segment, comprising the promoter—gene of interest—terminator plus selectable marker, flanked at both ends by host DNA sequences. This is conveniently accomplished by including 3' untranslated DNA sequence at the downstream end of the expression segment and relying on the promoter sequence at the 5' end. When using linear DNA, the expression segment will be flanked by cleavage sites to allow for linearization of the molecule and separation of the expression segment from other sequences (e.g., a bacterial origin of replication and selectable marker). Preferred such cleavage sites are those that are recognized by restriction endonucleases that cut infrequently within a DNA sequence, such as those that recognize 8-base target sequences (e.g., Not I).

Heterologous DNA is introduced into *P. methanolica* cells as disclosed above. A preferred method is electroporation. Electroporation of *P. methanolica* is preferably carried out on cells in early log phase growth. Cells are typically made electrocompetent by incubating them at about 30° C. for about 5 to 30 minutes in a buffered solution at pH 6–8 containing a reducing agent, such as dithiothreitol (DTT) or β-mercaptoethanol (BME), to reduce cell wall proteins to facilitate subsequent uptake of DNA. The cells are then harvested and washed in a suitable electroporation buffer, which is used ice-cold. Suitable buffers in this regard include pH 6–8 solutions containing a weak buffer, divalent cations (e.g., $Mg^{++}$, $Ca^{++}$) and an osmotic stabilizer (e.g., a sugar). A preferred electroporation buffer is STM (270 mM sucrose, 10 mM Tris, pH 7.5, 1 mM $MgCl_2$). Within a preferred protocol, the cells are subjected to two washes, first in the original culture volume of ice-cold buffer, then in one-half the original volume. Following the second wash, the cells are harvested and resuspended, typically using about 3–5 ml of buffer for an original culture volume of 200 ml.

Electroporation is carried out using a small volume of electrocompetent cells (typically about 100 μl) and up to one-tenth volume of linear DNA molecules. For example, 0.1 ml of cell suspension in a buffer not exceeding 50 mM in ionic strength is combined with 0.1–10 mg of DNA (vol. ≦10 ml). This mixture is placed in an ice-cold electroporation cuvette and subjected to a pulsed electric field of from 2.5 to 4.5 kV/cm, preferably about 3.75 kV/cm, and a time constant of about 20 milliseconds, with exponential decay. After being pulsed, the cells are diluted approximately 10× into 1 ml of YEPD broth and incubated at 30° C. for one hour.

The cells are then harvested and plated on selective media. Cells having an ade2 mutation that have been transformed with an ADE2 selectable marker can be plated on a minimal medium that lacks adenine, such as ADE D (Table 1) or ADE DS (Table 1). In a typical procedure, 250 ml aliqouts of cells are plated on 4 separate ADE D or ADE DS plates to select for Ade+cells.

For protein production, *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium is YEPD (Table 1). The cells may be passaged by dilution into fresh culture medium or stored for short periods on plates under refrigeration. For long-term storage, the cells are preferably kept in a 50% glycerol solution at −70° C.

TABLE 1

YEPD

2% D-glucose
2% Bacto ™ Peptone (Difco Laboratories, Detroit, MI)
1% Bacto ™ yeast extract (Difco Laboratories)
0.004% adenine
0.006% L-leucine

ADE D 0.056% -Ade-Trp-Thr powder
0.67% yeast nitrogen base without amino acids
2% D-glucose
0.5% 200X tryptophan, threonine solution

ADE DS 0.056% -Ade-Trp-Thr powder
0.67% yeast nitrogen base without amino acids
2% D-glucose
0.5% 200X tryptophan, threonine solution
18.22% D-sorbitol

LEU D 0.052% -Leu-Trp-Thr powder
0.67% yeast nitrogen base without amino acids
2% D-glucose
0.5% 200X tryptophan, threonine solution

HIS D 0.052% -His-Trp-Thr powder
0.67% yeast nitrogen base without amino acids
2% D-glucose
0.5% 200X tryptophan, threonine solution

URA D 0.056% -Ura-Trp-Thr powder
0.67% yeast nitrogen base without amino acids
2% D-glucose
0.5% 200X tryptophan, threonine solution

URA DS 0.056% -Ura-Trp-Thr powder
0.67% yeast nitrogen base without amino acids
2% D-glucose
0.5% 200X tryptophan, threonine solution
18.22% D-sorbitol TABLE 1-continued -Leu-Trp-Thr powder powder made by combining 4.0 g adenine, 3.0 g arginine, 5.0 g aspartic acid, 2.0 g histidine, 6.0 g isoleucine, 4.0 g lysine, 2.0 g methionine, 6.0 g phenylalanine, 5.0 g serine, 5.0 g tyrosine, 4.0 g uracil, and 6.0 g valine (all L-amino acids)

-His-Trp-Thr powder powder made by combining 4.0 g adenine, 3.0 g arginine, 5.0 g aspartic acid, 6.0 g isoleucine, 8.0 g leucine, 4.0 g lysine, 2.0 g methionine, 6.0 g phenylalanine, 5.0 g serine, 5.0 g tyrosine, 4.0 g uracil, and 6.0 g valine (all L-amino acids)

-Ura-Trp-Thr powder powder made by combining 4.0 g adenine, 3.0 g arginine, 5.0 g aspartic acid, 2.0 g histidine, 6.0 g isoleucine, 8.0 g leucine, 4.0 g lysine, 2.0 g methionine, 6.0 g phenylalanine, 5.0 g serine, 5.0 g tyrosine, and 6.0 g valine (all L-amino acids)

-Ade-Trp-Thr powder powder made by combining 3.0 g arginine, 5.0 g aspartic acid, 2.0 g histidine, 6.0 g isoleucine, 8.0 g leucine, 4.0 g lysine, 2.0 g methionine, 6.0 g phenylalanine, 5.0 g serine, 5.0 g tyrosine, 4.0 g uracil, and 6.0 g valine (all L-amino acids)

200X tryptophan, threonine solution 3.0% L-threonine, 0.8% L-tryptophan in $H_2O$ For plates, add 1.8% Bacto ™ agar (Difco Laboratories)

*P. methanolica* recognizes certain infrequently occuring sequences, termed autonomously replicating sequences (ARS), as origins of DNA replication, and these sequences may fortuitously occur within a DNA molecule used for transformation, allowing the transforming DNA to be maintained extrachromosomally. However, integrative transformants are generally preferred for use in protein production systems. Such cells can be propagated without continuous selective pressure because DNA is rarely lost from the genome. Integration of DNA into the host chromosome can be confirmed by Southern blot analysis. Briefly, transformed and untransformed host DNA is digested with restriction endonucleases, separated by electrophoresis, blotted to a support membrane, and probed with appropriate host DNA segments. Differences in the patterns of fragments seen in untransformed and transformed cells are indicative of integrative transformation. Restriction enzymes and probes can be selected to identify transforming DNA segments (e.g., promoter, terminator, heterologous DNA, and selectable marker sequences) from among the genomic fragments.

Differences in expression levels of heterologous proteins can result from such factors as the site of integration and copy number of the expression cassette and differences in promoter activity among individual isolates. It is therefore advantageous to screen a number of isolates for expression level prior to selecting a production strain. A variety of suitable screening methods are available. For example, transformant colonies are grown on plates that are overlayed with membranes (e.g., nitrocellulose) that bind protein. Proteins are released from the cells by secretion or following lysis, and bind to the membrane. Bound protein can then be assayed using known methods, including immunoassays. More accurate analysis of expression levels can be obtained by culturing cells in liquid media and analyzing conditioned media or cell lysates, as appropriate. Methods for concentrating and purifying proteins from media and lysates will be determined in part by the protein of interest. Such methods are readily selected and practiced by the skilled practitioner.

For small-scale protein production (e.g., plate or shake flask production), *P. methanolica* transformants that carry an expression cassette comprising a methanol-regulated promoter (such as the AUG1 promoter) are grown in the presence of methanol and the absence of interfering amounts of other carbon sources (e.g., glucose). For small-scale experiments, including preliminary screening of expression levels, transformants may be grown at 30° C. on solid media containing, for example, 20 g/L Bacto-agar (Difco), 6.7 g/L yeast nitrogen base without amino acids (Difco), 10 g/L methanol, 0.4 mg/L biotin, and 0.56 g/L of -Ade -Thr -Trp powder. Because methanol is a volatile carbon source it is readily lost on prolonged incubation. A continuous supply of methanol can be provided by placing a solution of 50% methanol in water in the lids of inverted plates, whereby the methanol is transferred to the growing cells by evaporative transfer. In general, not more than 1 mL of methanol is used per 100-mm plate. Slightly larger scale experiments can be carried out using cultures grown in shake flasks. In a typical procedure, cells are cultivated for two days on minimal methanol plates as disclosed above at 30° C., then colonies are used to inoculate a small volume of minimal methanol media (6.7 g/L yeast nitrogen base without amino acids, 10 g/L methanol, 0.4 mg/L biotin) at a cell density of about $1\times10^6$ cells/ml. Cells are grown at 30° C. Cells growing on methanol have a high oxygen requirement, necessitating vigorous shaking during cultivation. Methanol is replenished daily (typically 1/100 volume of 50% methanol per day).

For production scale culturing, fresh cultures of high producer clones are prepared in shake flasks. The resulting cultures are then used to inoculate culture medium in a fermenter. Typically, a 500 ml culture in YEPD grown at 30° C. for 1–2 days with vigorous agitation is used to inoculate a 5-liter fermenter. The cells are grown in a suitable medium containing salts, glucose, biotin, and trace elements at 28° C., pH 5.0, and >30% dissolved $O_2$. After the initial charge of glucose is consumed (as indicated by a decrease in oxygen consumption), a glucose/methanol feed is delivered into the vessel to induce production of the protein of interest. Because large-scale fermentation is carried out under conditions of limiting carbon, the presence of glucose in the feed does not repress the methanol-inducible promoter. The use of glucose in combination with methanol under glucose-limited conditions produces rapid growth, efficient conversion of carbon to biomass and rapid changes in physiological growth states, while still providing full induction of methanol-inducible gene e-promoters. In a typical fermentation run, a cell density of from about 80 to about 400 grams of wet cell paste per liter is obtained. "Wet cell paste" refers to the mass eof cells obtained by harvesting the cells from the fermentor, typically by centrifugation of the culture.

For large-scale, industrial processes where it is desirable to minimize the use of methanol, it is preferred to use host cells having a genetic defect in a gene required for methanol utilization. Such genes include the alcohol oxidase genes AUG1 and AUG2, as well as genes encoding catalase, formaldehyde dehydrogenase, formate dehydrogenase, dihydroxyacetone synthase, dihydroxyacetone kinase, fructose 1,6-bisphosphate aldolase, and fructose 1,6-bisphosphatase. It is particularly preferred to use cells in which both alcohol oxidase genes (AUG1 and AUG2) are deleted or otherwise altered to eliminate their activity. Such alteration can be achieved by the loop-in/loop-out method of the present invention or by targetted gene replacement.

The invention is further illustrated by the following, non-limiting examples.

EXAMPLES

Example 1

*P. methanolica* cells (strain CBS6515 from American Type Culture Collection, Rockville, Md.) were mutagenized by UV exposure. A killing curve was first generated by plating cells onto several plates at approximately 200–250 cells/plate. The plates were then exposed to UV radiation using a G8T5 germicidal lamp (Sylvania) suspended 25 cm from the surfaces of the plates for periods of time as shown in Table 2. The plates were then protected from visible light sources and incubated at 30° C. for two days.

TABLE 2

| | Viable Cells | | |
|---|---|---|---|
| Time | Plate 1 | Plate 2 | Average |
| 0 sec. | 225 | 229 | 227 |
| 1 sec. | 200 | 247 | 223 |
| 2 sec. | 176 | 185 | 181 |
| 4 sec. | 149 | 86 | 118 |
| 8 sec. | 20 | 7 | 14 |
| 16 sec. | 0 | 2 | 1 |

Large-scale mutagenesis was then carried out using a 2-second UV exposure to provide about 20% killing. Cells were plated at approximately $10^4$ cells/plate onto eight YEPD plates that were supplemented with 100 mg/L each of uracil, adenine, and leucine, which were added to supplement the growth of potential auxotrophs having the cognate deficiencies. Following UV exposure the plates were wrapped in foil and incubated overnight at 30° C. The following day the colonies on the plates (~$10^5$ total) were resuspended in water and washed once with water. An amount of cell suspension sufficient to give an $OD_{600}$ of 0.1–0.2 was used to inoculate 500 ml of minimal broth made with yeast nitrogen base without amino acids or ammonia, supplemented with 1% glucose and 400 μg/L biotin. The culture was placed in a 2.8 L baffled Bell flask and shaken vigorously overnight at 30° C. The following day the cells had reached an $OD_{600}$ of ~1.0–2.0. The cells were pelleted and resuspended in 500 ml of minimal broth supplemented with 5 g/L ammonium sulfate. The cell suspension was placed in a 2.8 L baffled Bell flask and shaken vigorously at 30° C. for 6 hours. 50 ml of the culture was set aside in a 250-ml flask as a control, and to the remainder of the culture was added 1 mg nystatin (Sigma Chemical Co., St. Louis, Mo.) to select for auxotrophic mutants (Snow, *Nature* 211:206–207, 1966). The cultures were incubated with shaking for an additional hour. The control and nystatin-treated cells were then harvested by centrifugation and washed with water three times. The washed cells were resuspended to an $OD_{600}$ of 1.0 in 50% glycerol and frozen. Titering of nystatin-treated cells versus the control cells for colony forming units revealed that nystatin enrichment had decreased the number of viable cells by a factor of $10^4$.

$10^{-2}$ dilutions of nystatin-treated cells were plated on 15 YEPD plates. Colonies were replica-plated onto minimal plates (2% agar, 1× YNB, 2% glucose, 400 μg/L biotin). The frequency of auxotrophs was about 2–4%. Approximately 180 auxotrophic colonies were picked to YEPD+Ade, Leu, Ura plates and replica-plated to various dropout plates. All of the auxotrophs were Ade⁻. Of these, 30 were noticably pink on dropout plates (LEU D, HIS D, etc.; see Table 1). Of the 30 pink mutants, 21 were chosen for further study; the remainder were either leaky for growth on ADE D plates or contaminated with wild-type cells.

The Ade⁻ mutants were then subjected to complementation analysis and phenotypic testing. To determine the number of loci defined by the mutants, all 21 mutants were mated to a single pink, Ade⁻ tester strain (strain #2). Mating was carried out by mixing cell suspensions ($OD_{600}$=1) and plating the mixtures in 10 μl aliquots on YEPD plates. The cells were then replicated to SPOR media (0.5w Na acetate, 1% KCl, 1% glucose, 1t agar) and incubated overnight at 30° C. The cells were then replica-plated to ADE D plates for scoring of phenotype. As shown in Table 3, some combinations of mutants failed to give Ade⁺ colonies (possibly defining the same genetic locus as in strain #2), while others gave rise to numerous Ade⁺ colonies (possibly defining a separate genetic locus). Because mutant #3 gave Ade⁺ colonies when mated to #2, complementation testing was repeated with mutant #3. If the group of mutants defined two genetic loci, then all mutants that failed to give Ade⁺ colonies when mated to strain #2 should give Ade⁺ colonies when mated to #3.

TABLE 3

| Mutant | × Mutant #2 | × Mutant #3 |
|---|---|---|
| #1 | + | − |
| #3 | + | − |
| #10 | + | − |
| #15 | + | − |
| #18 | + | − |
| #24 | + | − |
| #28 | + | − |
| #30 | + | − |
| #2 | − | + |
| #6 | − | + |
| #8 | − | + |
| #9 | − | + |
| #11 | − | + |
| #17 | − | + |
| #19 | − | + |
| #20 | − | + |
| #22 | − | + |
| #27 | − | + |
| #4 | + | + |
| #12 | + | + |
| #16 | + | + |

As shown in Table 3, most mutants fell into one of two groups, consistent with the idea that there are two adenine biosynthetic genes that, when missing, result in pink colonies on limiting adenine media. Three colonies (#4, #12, and #16) may either define a third locus or exhibit intragenic complementation. Two intensely pigmented mutants from each of the two complementation groups (#3 and #10; #6 and #11) were selected for further characterization. Additional analysis indicated that Ade⁻ was the only auxotrophy present in these strains.

A *P. methanolica* clone bank was constructed in the vector pRS426, a shuttle vector comprising 2μ and *S. cerevisiae* URA3 sequences, allowing it to be propagated in *S. cerevisiae*. Genomic DNA was prepared from strain CBS6515 according to standard procedures. Briefly, cells were cultured overnight in rich media, spheroplasted with zymolyase, and lysed with SDS. DNA was precipitated from the lysate with ethanol and extracted with a phenol/chloroform mixture, then precipitated with ammonium acetate and ethanol. Gel electrophoresis of the DNA preparation showed the presence of intact, high molecular weight DNA and appreciable quantities of RNA. The DNA was partially digested with Sau 3A by incubating the DNA in the presence of a dilution series of the enzyme. Samples of the digests were analyzed by electrophoresis to determine the size distribution of fragments. DNA migrating between 4 and 12 kb was cut from the gel and extracted from the gel slice. The size-fractionated DNA was then ligated to pRS426 that had been digested with Bam HI and treated with alkaline phosphatase. Aliquots of the reaction mixture were electroporated in *E. coli* MC1061 cells using a BioRad Gene Pulser™ device as recommended by the manufacturer.

The genomic library was used to transform *S. cerevisiae* strain HBY21A (ade2 ura3) by electroporation (Becker and Guarente, *Methods Enzymol.* 194:182–187, 1991). The cells were resuspended in 1.2 M sorbitol, and six 300-µl aliquots were plated onto ADE D, ADE DS, URA D and URA DS plates (Table 1). Plates were incubated at 30° C. for 4–5 days. No Ade$^+$ colonies were recovered on the ADE D or ADE DS plates. Colonies from the URA D and URA DS plates were replica-plated to ADE D plates, and two closely spaced, white colonies were obtained. These colonies were restreaked and confirmed to be Ura$^+$ and Ade$^+$. These two strains, designated Ade1 and Ade6, were streaked onto media containing 5 FOA (5 fluoro orotic acid; Sikorski and Boeke, *Methods Enzymol.* 194:302–318). Ura$^-$ colonies were obtained, which were found to be Ade$^-$ upon replica plating. These results indicate that the Ade$^+$ complementing activity is genetically linked to the plasmid-borne URA3 marker. Plasmids obtained from yeast strains Ade1 and Ade6 appeared to be identical by restriction mapping as described below. These genomic clones were designated pADE1-1 and pADE1-6, respectively.

Total DNA was isolated from the HBY21A transformants Ade1 and Ade6 and used to transform *E. coli* strain MC1061 to Amp$^R$. DNA was prepared from 2 Amp$^R$ colonies of Ade1 and 3 Amp$^R$ colonies of Ade6. The DNA was digested with Pst I, Sca I, and Pst I+Sca I and analyzed by gel electrophoresis. All five isolates produced the same restriction pattern.

PCR primers were designed from the published sequence of the *P. methanolica* ADE2 gene (also known as ADE1; Hiep et al., *Yeast* 9:1251–1258, 1993). Primer ZC9080 (SEQ ID NO:4) was designed to prime at bases 406–429 of the ADE2 DNA (SEQ ID NO:1), and primer ZC9079 (SEQ ID NO:5) was designed to prime at bases 2852–2829. Both primers included tails to introduce Avr II and Spe I sites at each end of the amplified sequence. The predicted size of the resulting PCR fragment was 2450 bp.

PCR was carried out using plasmid DNA from the five putative ADE2 clones as template DNA. The 100 ml reaction mixtures contained 1× Taq PCR buffer (Boehringer Mannheim, Indianapolis, Ind.), 10–100 ng of plasmid DNA, 0.25 mM dNTPs, 100 pmol of each primer, and 1 µl Taq polymerase (Boehringer Mannheim). PCR was run for 30 cycles of 30 seconds at 94° C., 60 seconds at 50° C., and 120 seconds at 72° C. Each of the five putative ADE2 genomic clones yielded a PCR product of the expected size (2.4 kb). Restriction mapping of the DNA fragment from one reaction gave the expected size fragments when digested with Bgl II or Sal I.

The positive PCR reactions were pooled and digested with Spe I. Vector pRS426 was digested with Spe I and treated with calf intestinal phosphatase. Four µl of PCR fragment and 1 µl of vector DNA were combined in a 10 µl reaction mix using conventional ligation conditions. The ligated DNA was analyzed by gel electrophoresis. Spe I digests were analyzed to identify plasmids carrying a subclone of the ADE2 gene within pRS426. The correct plasmid was designated pCZR118.

Because the ADE2 gene in pCZR118 had been amplified by PCR, it was possible that mutations that disabled the functional character of the gene could have been generated. To test for such mutations, subclones with the desired insert were transformed singly into *Saccharomyces cerevisiae* strain HBY21A. Cells were made electrocompetent and transformed according to standard procedures. Transformants were plated on URA D and ADE D plates. Three phenotypic groups were identified. Clones 1, 2, 11, and 12 gave robust growth of many transformants on ADE D. The transformation frequency was comparable to the frequency of Ura$^+$ transformants. Clones 6, 8, 10, and 14 also gave a high efficiency of transformation to both Ura$^+$ and Ade$^+$, but the Ade$^+$ colonies were somewhat smaller than those in the first group. Clone 3 gave many Ura$^+$ colonies, but no Ade$^+$ colonies, suggesting it carried a non-functional ade2 mutation. Clones 1, 2, 11, and 12 were pooled.

To identify the *P. methanolica* ade2 complementation group, two representative mutants from each complementation group (#3 and #10; #6 and #11), which were selected on the basis of deep red pigmentation when grown on limiting adenine, were transformed with the cloned ADE gene. Two hundred ml cultures of early log phase cells were harvested by centrifugation at 3000× g for 3 minutes and resuspended in 20 ml of fresh KD buffer (50 mM potassium phosphate buffer, pH 7.5, containing 25 mM DTT). The cells were incubated in this buffer at 30° C. for 15 minutes. The cells were then harvested and resuspended in 200 ml of ice-cold STM (270 mM sucrose, 10 mM Tris, pH 7.5, 1 mM MgCl$_2$). The cells were harvested and resuspended in 100 ml of ice-cold STM. The cells were again harvested and resuspended in 3–5 ml of ice-cold STM. 100-µl aliqouts of electrocompetent cells from each culture were then mixed with Not I-digested pADE1-1 DNA. The cell/DNA mixture was placed in a 2 mm electroporation cuvette and subjected to a pulsed electric field of 5 kV/cm using a BioRad Gene Pulser™ set to 1000 Ω resistance and capacitance of 25 µF. After being pulsed, the cells were diluted by addition of 1 ml YEPD and incubated at 30° C. for one hour. The cells were then harvested by gentle centrifugation and resuspended in 400 µl minimal selective media lacking adenine (ADE D). The resuspended samples were split into 200-µl aliqouts and plated onto ADE D and ADE DS plates. Plates were incubated at 30° C. for 4–5 days. Mutants #6 and #11 gave Ade$^+$ transformants. No Ade$^+$ transformants were observed when DNA was omitted, hence the two isolates appeared to define the ade2 complementation group. The ADE2 sequence is shown in SEQ ID NO:1.

Example 2

Figure 2:
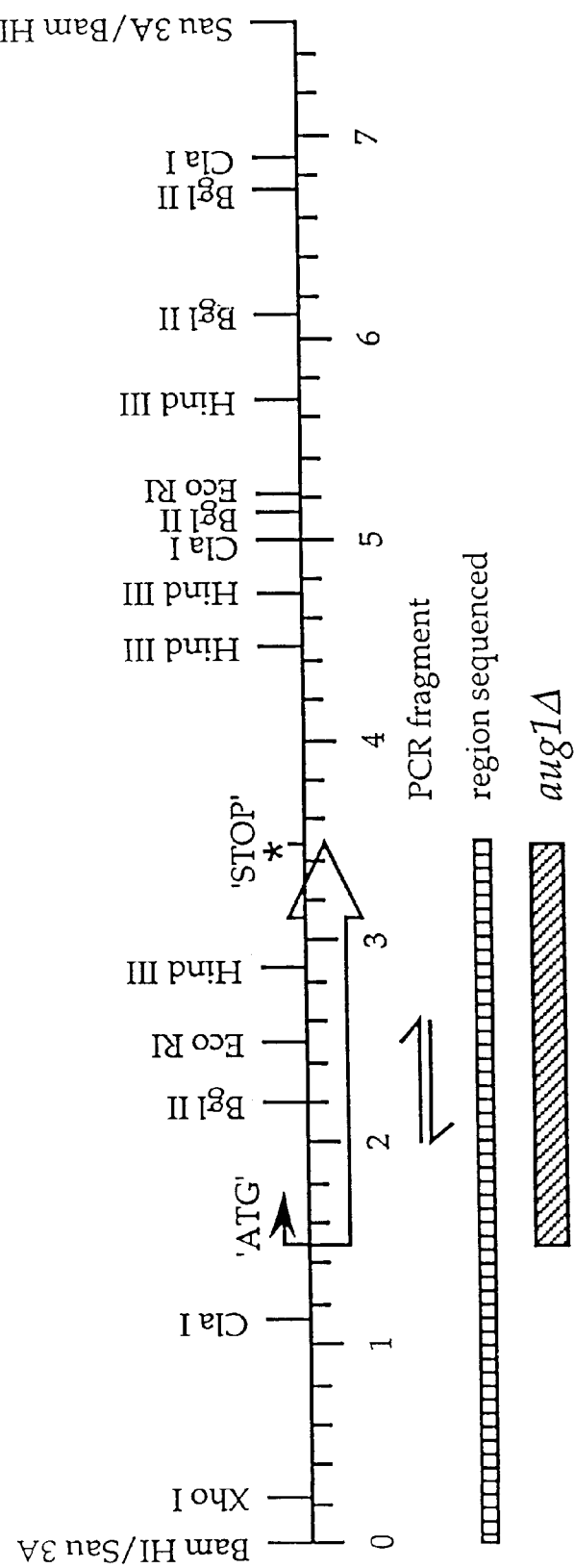
FIG. 2 shows a partial restriction map of a *P. methanolica* alcohol oxidase (AUG1) gene. The open arrow indicates the open reading frame. The locations of the original PCR product, sequenced region, and gene deletion are shown.

The *P. methanolica* clone bank disclosed in Example 1 was used as a source for cloning the Alcohol Utilization Gene (AUG1). The clone bank was stored as independent pools, each representing about 200–250 individual genomic clones. 0.1 ml of "miniprep" DNA from each pool was used as a template in a polymerase chain reaction with PCR primers (ZC8784, SEQ ID NO:6; ZC8787, SEQ ID NO:7) that were designed from an alignment of conserved sequences in alcohol oxidase genes from *Hansenula polymorpha*, *Candida boidini*, and *Pichia pastoris*. The amplification reaction was run for 30 cycles of 94° C., 30 seconds; 50° C., 30 seconds; 72° C., 60 seconds; followed by a 7 minute incubation at 72° C. One pool (#5) gave a ~600 bp band (FIG. 2). DNA sequencing of this PCR product revealed that it encoded an amino acid sequence with ~70% sequence identity with the *Pichia pastoris* alcohol oxidase encoded by the AOX1 gene and about 85% sequence identity with the *Hansenula polymorpha* alcohol oxidase encoded by the MOX1 gene. The sequence of the cloned AUG1 gene is shown in SEQ ID NO:2.

Sub-pools of pool #5 were analyzed by PCR using the same primers used in the initial amplification. One positive sub-pool was further broken down to identify a positive colony. This positive colony was streaked on plates, and DNA was prepared from individual colonies. Three colonies gave identical patterns after digestion with Cla I.

Restriction mapping of the genomic clone and PCR product revealed that the AUG1 gene lay on a 7.5 kb genomic insert and that sites within the PCR fragment could be uniquely identified within the genomic insert (FIG. 2). Because the orientation of the gene within the PCR fragment was known, the latter information provided the approximate location and direction of transcription of the AUG1 gene within the genomic insert. DNA sequencing within this region revealed a gene with very high sequence similarity at the amino acid level to other known alcohol oxidase genes.

Example 3

To generate a *P. methanolica* strain deficient for vacuolar proteases, the PEP4 and PRB1 genes were identified and disrupted. PEP4 and PRB1 sequences were amplified by PCR in reaction mixtures containing 100 pmol of primer DNA, 1× buffer as supplied (Boehringer Mannheim, Indianapolis, Ind.), 250 mM dNTPs, 1–100 pmol of template DNA, and 1 unit of Taq polymerase in a reaction volume of 100 ml. The DNA was amplified over 30 cycles of 94° C., 30 seconds; 50° C., 60 seconds; and 72° C., 60 seconds.

Using an alignment of PEP4 sequences derived from *S. cerevisiae* (Ammerer et al., *Mol. Cell. Biol.* 6:2490–2499, 1986; Woolford et al., *Mol. Cell. Biol.* 6:2500–2510, 1986) and *P. pastoris* (Gleeson et al., U.S. Pat. No. 5,324,660), several sense and antisense primers corresponding to conserved regions were designed. One primer set, ZC9118 (SEQ ID NO:8) and ZC9464 (SEQ ID NO:9) produced a PCR product of the expected size from genomic DNA, and this set was used to identify a genomic clone corresponding to the amplified region. DNA sequencing of a portion of this genomic clone (shown in SEQ ID NO:10) revealed an open reading frame encoding a polypeptide with 70% amino acid identity with proteinase A from *S. cerevisiae* (SEQ ID NO:11).

Primers for the identification of *P. methanolica* PRB1 were designed on the basis of alignments between the PRB1 genes of *S. cerevisiae* (Moehle et al., *Mol. Cell. Biol.* 7:4390–4399, 1987), *P. pastoris* (Gleeson et al., U.S. Pat. No. 5,324,660), and *Kluyveromyces lactis* (Fleer et al., WIPO Publication WO 94/00579). One primer set, ZC9126 (SEQ ID NO:12) and ZC9741 (SEQ ID NO:13) amplified a ca. 400 bp fragment from genomic DNA (SEQ ID NO:14). This product was sequenced and found to encode a polypeptide with 70% amino acid identity with proteinase B from *S. cerevisiae* (SEQ ID NO:15). The PRB primer set was then used to identify a genomic clone encompassing the *P. methanolica* PRB1 gene.

Figure 3:
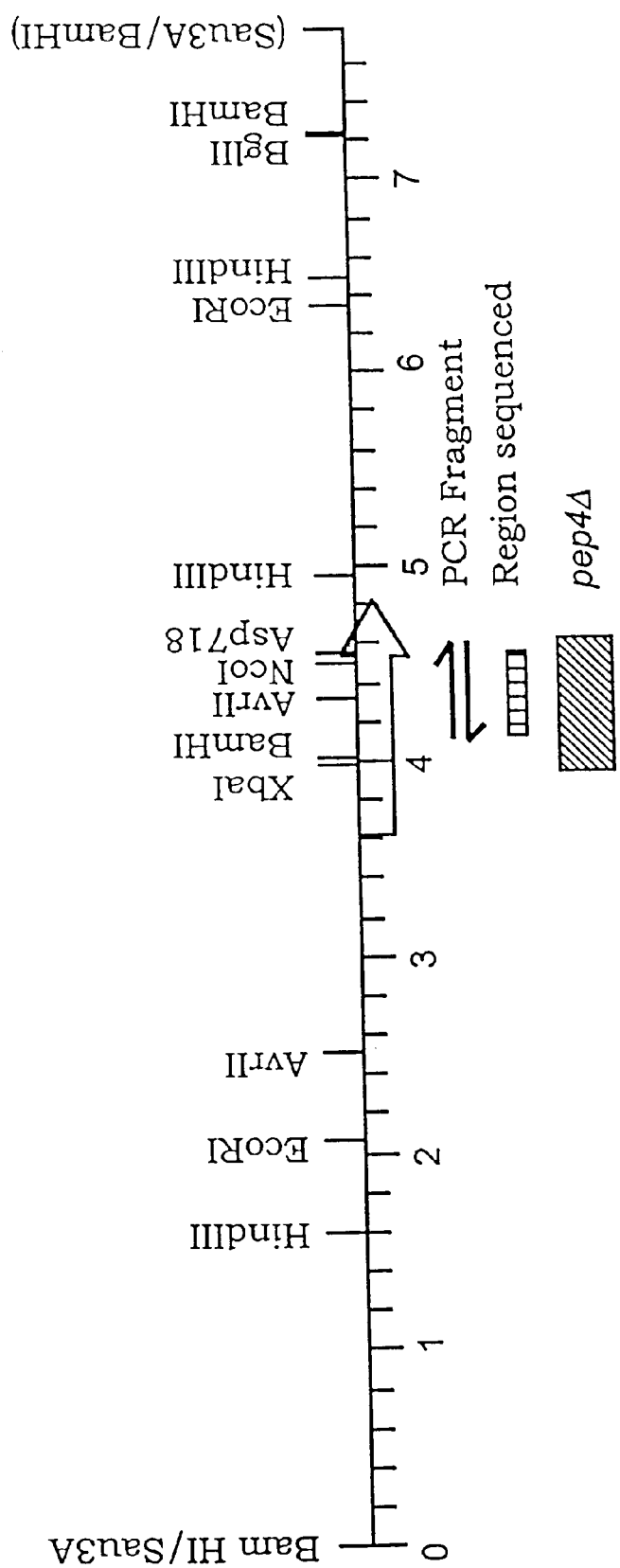
FIG. 3 shows a partial restriction map of a genomic clone comprising a *P. methanolica* PEP4 gene. The PCR product used to identify the gene is shown as complementary half arrows. A 420 bp fragment left of the Asp718 site was sequenced. The pep4Δ allele was created by deleting the indicated region between the BamHI and NcoI sites.
Figure 4:
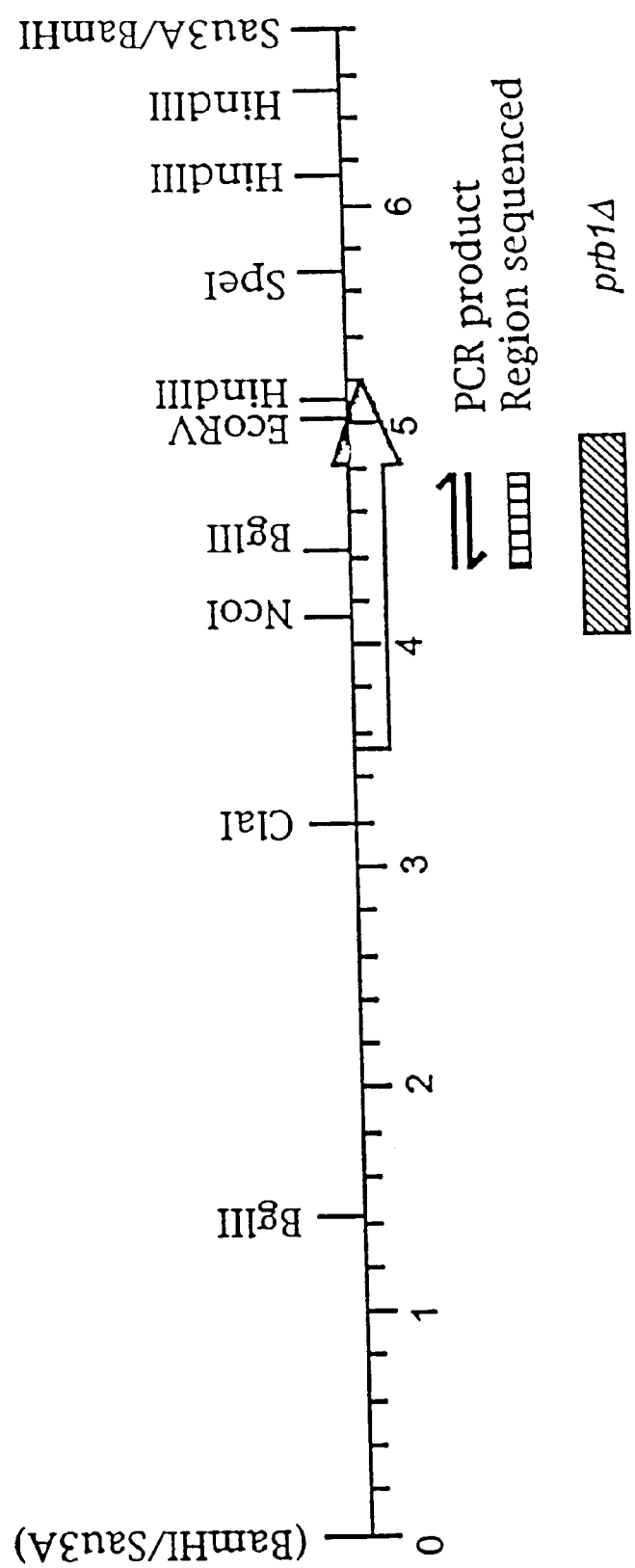
FIG. 4 shows a partial restriction map of a genomic clone comprising a *P. methanolica* PRB1 gene. The PCR product used to identify the gene is shown as complementary half arrows. The prb1Δ allele was generated by deleting the indicated region between the NcoI and EcoRV sites.

Deletion mutations in the *P. methanolica* PEP4 and PRB1 genes were generated using available restriction enzyme sites. The cloned genes were restriction mapped. The pep4Δ allele was created by deleting a region of approximately 500 bp between BamHI and NcoI sites (FIG. 3) and including nucleotides 1 through 393 of the sequence shown in SEQ ID NO:10. The prb1Δ allele was generated by deleting a region of approximately 1 kbp between NcoI and EcoRV sites (FIG. 4) and including the sequence shown in SEQ ID NO:14. The cloned PEP4 and PRB1 genes were subcloned into pCZR139, a phagemid vector (pBluescript® II KS(+), Stratagene, La Jolla, Calif.) that carried a 2.4 kb SpeI ADE2 insert, to create the deletions. In the case of PEP4 gene, the unique BamHI site in pCZR139 was eliminated by digestion, fill-in, and religation. The vector was then linearized by digestion with EcoRI and HindIII, and a ca. 4 kb EcoRI-HindIII fragment spanning the PEP4 gene was ligated to the linearized vector to produce plasmid pCZR142. A ca. 500 bp deletion was then produced by digesting pCZR142 with BamHI and NcoI, filling in the ends, and religating the DNA to produce plasmid pCZR143. The PRB1 gene (~5 kb XhoI-BamHI fragment) was subcloned into pCZR139, and an internal EcoRV-NcoI fragment, comprising the sequence shown in SEQ ID NO:14, was deleted to produce plasmid pCZR153.

Plasmid pCZR143 was linearized with Asp718, which cut at a unique site. The linearized plasmid was introduced into the *P. methanolica* PMAD11 strain (an ade2 mutant generated as disclosed in Example 1). Transformants were grown on ADE DS (Table 1) to identify Ade$^+$ transformants. Two classes of white, Ade$^+$ transformants were analyzed. One class arose immediately on the primary transformation plate; the second became evident as rapidly growing white papillae on the edges of unstable, pink transformant colonies.

Southern blotting was used to identify transformants that had undergone the desired homologous integration event. 100 ml of cell paste was scraped from a 24–48 hour YEPD plate and washed in 1 ml water. Washed cells were resuspended in 400 ml of spheroplast buffer (1.2 M sorbitol, 10 mM Na citrate pH 7.5, 10 mM EDTA, 10 mM DTT, 1 mg/ml zymolyase 100T) and incubated at 37° C. for 10 minutes. Four hundred ml of 1% SDS was added, the cell suspension was mixed at room temperature until clear, 300 ml of 5 M potassium acetate was mixed in, and the mixture was clarified by microcentrifugation for 5 minutes. 750 ml of the clarified lysate was extracted with an equal volume of phenol:chloroform:isoamyl alcohol (25:24:1), 600 ml was transferred to a fresh tube, 2 volumes of 100% ethanol was added, and the DNA was precipitated by microcentrifugation for 15 minutes at 4° C. The pellet was resuspended in 50 ml of TE (10 mM Tris pH 8.0, 1 mM EDTA) containing 100 mg/ml of RNAase A. Ten ml of DNA (approximately 100 ng) was digested in 100 ml total volume with appropriate enzymes, precipitated with 200 ml ethanol, and resuspended in 10 ml of DNA loading dye. The DNA was separated in 0.7% agarose gels and transferred to nylon membranes (Nytran N$^+$, Amersham Corp., Arlington Heights, Ill.) in a semi-dry blotting apparatus (BioRad Laboratories, Richmond, Calif.) as recommended by the manufacturer. Transferred DNA was denatured, neutralized, and cross-linked to the membrane with UV light using a Stratalinker (Stratagene, La Jolla, Calif.). To identify strains with a tandem integration at PEP4, two probes were used. One was a 1400 bp EcoRI-HindIII fragment from the 3' end of PEP4. The second was a 2000 bp BamHI-EcoRI fragment from the 5' end of PEP4. Fragments were detected using chemiluminescence reagents (ECL™ direct labelling kit; Amersham Corp., Arlington Heights, Ill.).

Parent strains harboring a tandem duplication of the wild-type and deletion alleles of the gene were grown in YEPD broth overnight to allow for the generation of looped-out, Ade strains. These cells were then plated at a density of 2000–5000 colonies per plate on adenine-limited YEPD plates, grown for 3 days at 30° C. and 3 days 3at room temperature. The shift to room temperature enhanced pigmentation of rare, pink, Ade$^-$ colonies. Loop-out strains were consistently detected at a frequency of approximately one pink, Ade$^-$ colony per 10,000 colonies screened. These strains were screened for retention of the wild-type or mutant genes by Southern blotting or by PCR using primers that spanned the site of the deletion. An ade2-11 pep4Δ strain was designated PMAD15.

The PRB1 gene was then deleted from PMAD15 essentially as described above by transformation with plasmid pCZR153. Blots were probed with PCR-generated probes for internal portions of the PRB1 and ADE2 genes. The PRB1 probe was generated by subcloning a 2.6 kb ClaI-SpeI fragment of PRB1 into the phagemid vector pBluescript® II KS(+) to produce pCZR150, and amplifying the desired region by PCR using primers ZC447 (SEQ ID NO: 16) and ZC976 (SEQ ID NO: 17). The ADE2 probe was generated by amplifying the ADE2 gene in pCZR139 with primers ZC9079 (SEQ ID NO:5) and ZC9080 (SEQ ID NO:4) The resulting ade2-11 pep4Δ prb1Δ strain was designated PMAD16.

The effects of the pep4Δ and pep4Δ prb1Δ mutations on vacuolar protease activity were determined using the APNE overlay assay (Wolf and Fink, *J. Bacteriol.* 123:1150–1156, 1975; Jones, *Methods Enzymol.* 194:428–453, 1991). Protease proficient colonies become red upon addition of the overlay, while mutants devicient in vacuolar protease activity remain white. PMAD11 and PMAD15 colonies produced a bright red color. In is contrast, colonies of PMAD16 remained white. While not wishing to be bound by theory, the Pep+ phenotype of the pep4Δ mutant may have been a consequence of phenotypic lag or the capability of the *P. methanolica* proteinase B for autoactivation. However, the pep4Δ prb1Δ strain possessed the desired protease-deficient phenotype.

Example 4

An aug1Δ mutation was generated in *P. methanolica* strain PMAD11. A genomic AUG1 clone is shown in FIG. 2 and SEQ ID NO:2. A deletion allele was made by joining the 1350 bp AUG1 promoter to the 1600 bp AUG1 terminator and 3' untranslated sequence as shown in FIG. 2. A linear DNA construct comprising the deletion allele and an ADE2 selectable marker was electroporated into PMAD11, and Ade+ transformants were selected essentially as disclosed in Example 3. Homologous recombinants were identified by Southern blotting. Ade+ auxotrophs in which the AUG1 locus was duplicated were cultured in YEPD broth overnight, then transferred to YEPD plates. Pink colonies were picked and screened for looping out of the wild type locus by Southern blotting and PCR.

The aug1Δ mutant strain, designated PMAD12, grew poorly in minimal methanol broth. On minimal methanol plates, PMAD12 exhibited a slight growth defect relative to wild-type cells. These data suggest that the Aug1 protein plays an important role in methanol assimilation, particularly in liquid media, but that *P. methanolica* possesses a second alcohol oxidase activity.

Example 5

A second alcohol oxidase gene was identified in *P. methanolica* using alcohol oxidase-specific PCR primers to amplify genomic DNA from an aug1Δ mutant strain. A weak, 600 bp signal was detected, which was reamplified and subjected to DNA sequencing (SEQ ID NO:3). Translation of this sequence and alignment with the Aug1 sequence showed an 83% identity with the corresponding region of the Aug1 protein. The PCR fragment was then used as a probe to identify a full-length clone for this second alcohol oxidase gene, which was designated AUG2 (FIG. 5).

Figure 5:
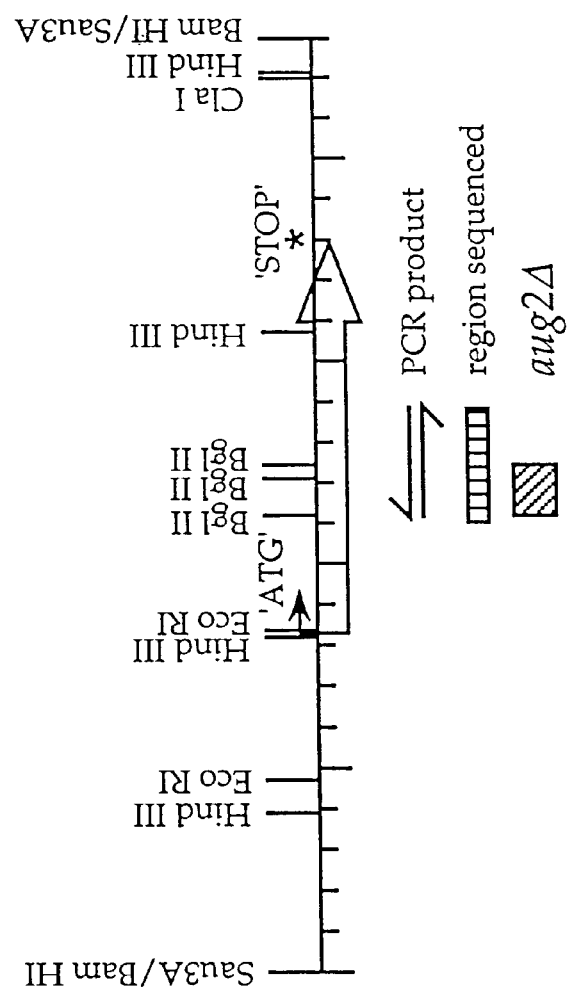
FIG. 5 illustrates a partial restriction map of a second *P. methanolica* alcohol oxidase (AUG2) gene. The open arrow indicates the open reading frame. The position of the stop codon was estimated based on the lengths of other known alcohol oxidase coding regions. The locations of the original PCR product, sequenced region, and gene deletion are shown.

A disrupted allele of the AUG2 gene was constructed as shown in FIG. 5 by deleting the two BglII fragments within the open reading frame.

The aug2Δ mutant allele was combined with the ADE2 selectable marker, and resulting linear construct was introduced into *P. methanolica* strains PMAD11, PMAD12 and (aug1Δ). The resulting deletion mutants PMAD13 (aug2Δ) and PMAD14 (aug1Δ aug2Δ) were selected and identified essentially as disclosed in Examples 3 and 4. These isogenic strains were cultured on minimal methanol broth and minimal methanol plates. The double mutant was unable to grow on minimal methanol media of any kind, indicating that the AUG1 and AUG2 genes are the only alcohol oxidase genes in *P. methanolica*. While the aug1Δ strain grew poorly in minimal methanol broth, the aug2Δ mutant comparably to wild-type cells. These data suggest that the Aug1 protein plays a major role in the utilization of methanol during growth in liquid cultures. When grown on plates, the growth differential between aug1Δ and aug2Δ mutants was much less pronounced. Examination of total cell extracts by SDS-PAGE showed that AUG2 protein was strongly induced in aug1Δ cells grown on plates, but it was poorly expressed in shake flask cultures or in cells grown under methanol-induced fermentation conditions.

Example 6

Figure 6:
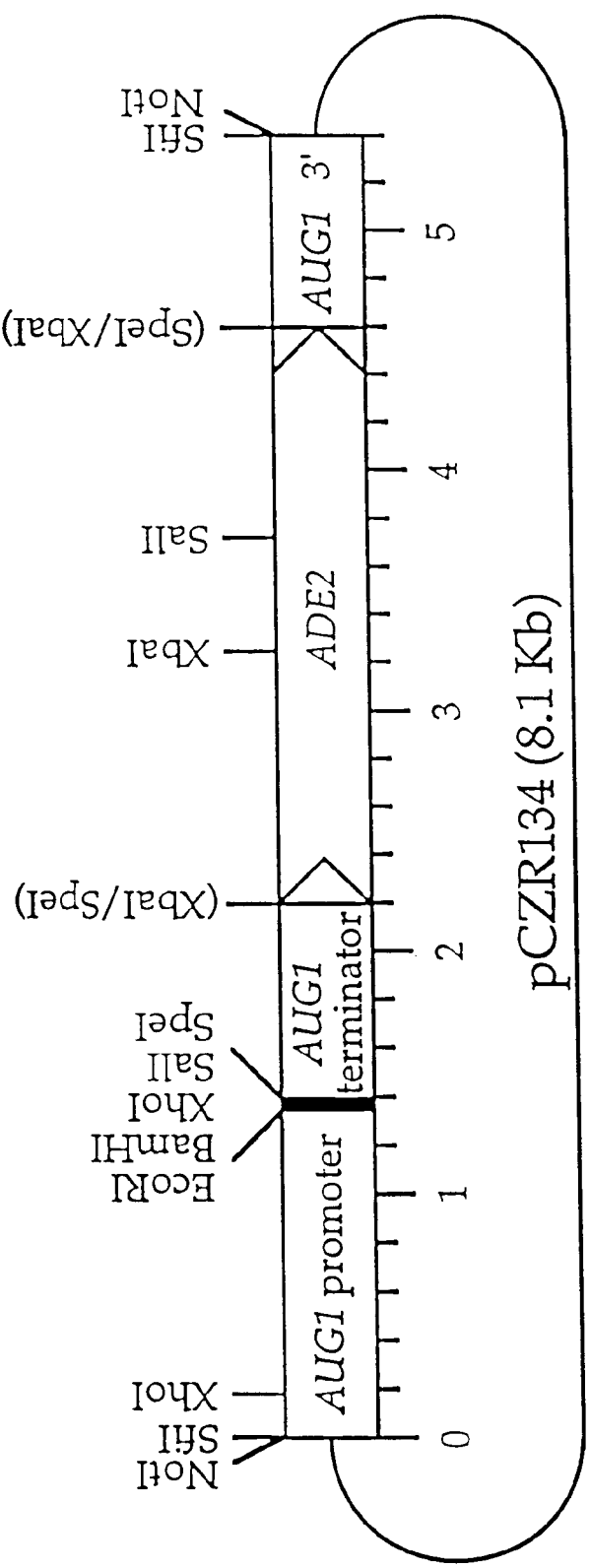
FIG. 6 illustrates the plasmid pCZR134.

A human glutamic acid decarboxylase ($GAD_{65}$) expression vector was constructed by inserting the cDNA encoding human $GAD_{65}$ (Karlsen et al., *Proc. Natl. Acad. Sci. USA* 88:8337–8341, 1991) as an EcoRI-XbaI fragment into the EcoRI-SpeI sites of plasmid pCZR134 (FIG. 6). The resulting expression vector, pCZR137, comprised the AUG1 promoter and terminator and ADE2 selectable marker.

Plasmid pCZR137 was digested with NotI and used to transform PMAD16 to Ade+. One thousand stable Ade+ transformants were screened for $GAD_{66}$ expression on minimal methanol plates using a nitrocellulose overlay, colony lysis and western blot technique essentially as disclosed by Wuestehube et al., *Genetics* 142:393–406, 1996. Transformants were patched in grids of 50 to minimal plates lacking adenine, grown for 24 hours at 30° C., replica plated to minimal methanol plates, overlayed with nitrocellulose, and incubated for at least 48 hours at 30° C. Filters were removed from plates and placed colony side up for 30 minutes at room temperature on filter paper saturated with lysis buffer (0.1% SDS, 0.2 N NaOH, 35 mM DTT). Debris was rinsed from the filters under a stream of distilled water, and the filters were neutralized by a 5-minute incubation in 0.1 M acetic acid. The filters were then blocked in TTBS-NFM (20 mM Tris pH 7.4, 160 mM NaCl, 0.1% Tween 20, 5% non-fat milk) and incubated in TTBS-NFM containing the human $GAD_{65}$-specific monoclonal antibody GAD6 (Chang and Gottlieb, *J. Neurosci.* 8:2123–2130, 1988). Horseradish peroxidase-conjugated goat anti-mouse antibody was used to detect GAD65-specific immune complexes, which were visualized with commercially available chemiluminescence reagents (ECL™; Amersham Inc., Arlington Heights, Ill.) according to conventional techniques.

Ninety percent of the transformants were found to express $GAD_{65}$. Forty-six strains that appeared to express the highest levels of $GAD_{65}$ were reassayed by SDS-PAGE/western analysis. Forty-four of these strains appeared to make identical levels of $GAD_{65}$. Southern blot analysis (essentially as disclosed in Example 3) indicated that these strains carried a single copy of the $GAD_{65}$ expression cassette. Two strains appeared to make elevated levels of $GAD_{65}$. Both of these strains exhibited sluggish growth in minimal methanol broth, and analysis of genomic DNA from these strains by PCR using primers specific for AUG1 revealed that these strains were aug1Δ, indicating that transplacement of the wild-type AUG1 gene by the $GAD_{65}$ expression cassette had occurred. The aug1Δ strain making the highest apparent levels of $GAD_{65}$, PGAD4-2, was cultured under high cell density fermentation conditions in a BioFlow 3000 fermentor (New Brunswick Scientific Co., Inc., Edison, N.J.). An inoculum was generated by suspending cells from a 2-day YEPD plate in 250 ml of YEPD broth, and the culture was shaken vigorously overnight in a 1-liter baffled flask at 30° C. The fermentation vessel was charged with 2.5 liters of media containing 57.8 g $(NH_4)_2SO_4$, 46.6 g KCl, 30.8 g $MgSO_4.7H_2O$, 8.6 g $CaSO_4.2H_2O$, 2.0 g NaCl, and 10 ml of antifoam. After autoclaving and cooling of the vessel to a working temperature of 29° C., 350 ml of 50% glucose, 210 ml of 30% sodium hexametaphosphate (phosphate glass), and 250 ml of trace elements (containing, per liter, 27.8 g $FeSO_4.7H_2O$, 0.5 g $CuSO_4.5H_2O$, 1.09 g $ZnCl_2$, 1.35 g $MnSO_4.H_2O$, 0.48 g $CoCl_2.6H_2O$, 0.24 g $Na_2MoO_4.2H_2O$, 0.5 g $H_3BO_3$, 0.08 g KI, 5 mg biotin, 0.5 g thiamine, and 2.5 ml $H_2SO_4$) were added. The pH of the fermentor was adjusted to 5.0 and controlled automatically with 10% $NH_4OH$ and 10% $H_3PO_4$. Aeration was provided initially as compressed air provided at a flow rate of 5 liters/minute and an impeller agitation rate of 300 rpm. After dissolved oxygen was set to 100%, the cell inoculum was added. Dissolved oxygen control was set to be maintained at 30% of saturation within and agitation range of 300–800 rpm. Oxygen demand above 800 rpm activated automatic supplementation with pure oxygen. The batch phase of growth was characterized by a steady increase in demand over a 24–36 hour period. Following exhaustion of glucose, the oxygen demand fell rapidly, and a glucose feed (containing, per 1.5 liter, 750 g glucose, 110 g $(NH_4)_2SO_4$, and 278 ml trace elements) was initiated at a rate of 0.4% glucose/hour. After 25 hours, the transtition to methanol induction of the AUG1 promoter was made with a mixed feed of glucose (0.2%/hour) and methanol (0.2%/hour) for 5 hours. A final mixed methanol feed (0.1% glucose/hour, 0.4% methanol/hour) was run for 25 hours. Robust $GAD_{65}$ expression was induced by the addition of methanol. The expression level of $GAD_{65}$ was calculated to be about 500 mg/L in a final cell mass of 170 grams wet cell paste/L.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for altering a chromosomal locus of *Pichia methanolica* cells, comprising:

(a) selecting a target chromosomal locus of said cells;

(b) providing a population of *P. methanolica* cells each comprising a chromosomal copy of said locus, wherein said cells are auxotrophic for adenine;

(c) introducing into said provided cells a linear DNA construct comprising (i) a segment comprising a portion of said target chromosomal locus in which at least one nucleotide pair is altered, and (ii) a selectable marker that complements adenine auxotrophy;

(d) culturing said cells from step (c) under conditions that are selective for the presence in said cells of said selectable marker;

(e) identifying a subset of said cultured cells in which said segment of said DNA construct and said selectable marker have been chromosomally integrated by homologous recombination, said recombination resulting in tandem duplication of said target chromosomal locus;

(f) culturing said identified subset of cells under conditions wherein cells prototrophic for adenine grow and exhibit a first phenotype, and cells auxotrophic for adenine grow and exhibit a second phenotype;

(g) recovering cells that are auxotrophic for adenine; and (h) identifying a subset of said auxotrophic cells in which said segment of said DNA construct has been chromosomally integrated, whereby the target chromosomal locus is altered.

2. The method of claim 1 wherein a plurality of nucleotide pairs of said portion of said chromosomal locus are altered in said segment.

3. The method of claim 1 wherein from 1 kbp to 2 kbp of said portion of said chromosomal locus is altered in said segment.

4. The method of claim 1 wherein said at least one nucleotide pair is altered by deletion.

5. The method of claim 1 wherein said target chromosomal locus encodes a protease.

6. The method of claim 5 wherein said protease is proteinase A or proteinase B.

7. The method of claim 1 wherein said target chromosomal locus encodes an alcohol oxidase.

8. The method of claim 1 wherein steps (a) through (h) are repeated, whereby two chromosomal loci are altered.

9. The method of claim 8 wherein one of said two chromosomal loci encodes a protease, and a second of said two chromosomal loci encodes an alcohol oxidase.

10. The method of claim 1 wherein said target chromosomal locus is a nutritional marker.

11. The method of claim 1 wherein said selectable marker comprises nucleotides 407–2851 of SEQ ID NO:1.

* * * * *

UNITED STATES PATENT AND TRADEMARK OFFICE
CERTIFICATE OF CORRECTION

PATENT NO. : 6,183,953 B1
DATED : February 6, 2001
INVENTOR(S) : Christopher K. Raymond It is certified that error appears in the above-identified patent and that said Letters Patent is hereby corrected as shown below:

Column 10,
Line 64, delete "31" and insert therefor, -- 3' --.

Column 14,
Line 48, delete "e-promoters" and insert therefor, -- promoters --.
Line 51, delete "eof" and insert therefor, -- of --.

Column 16,
Line 7, delete "0.5w" and insert therefor, -- 0.5% --.
Line 8, delete "1t" and insert therefor, -- 1% --.

Column 20,
Line 60, delete "Ade" and insert therefor, -- Ade --.
Line 62, delete "3at" and insert therefor, -- at --.

Column 21,
Line 22, delete "devicient" and insert therefor, -- deficient --.

Column 22,
Line 33, delete "$GAD_{66}$" and insert therefor, -- $GAD_{65}$ --.

Signed and Sealed this

Fifth Day of March, 2002

Attest:

*Attesting Officer*

JAMES E. ROGAN
*Director of the United States Patent and Trademark Office*